US008680153B2

(12) United States Patent
Radzioch et al.

(10) Patent No.: US 8,680,153 B2
(45) Date of Patent: Mar. 25, 2014

(54) METHOD FOR CORRECTING A LIPID IMBALANCE IN A SUBJECT

(75) Inventors: Danuta Radzioch, Saint-Laurent (CA); Claudine Guilbault, Saint-Jean sur Richelieu (CA); Juan Bautista De Sanctis, Caracas (VE)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 564 days.

(21) Appl. No.: 12/097,229

(22) PCT Filed: Dec. 13, 2006

(86) PCT No.: PCT/CA2006/002041
§ 371 (c)(1),
(2), (4) Date: Jun. 12, 2008

(87) PCT Pub. No.: WO2007/068116
PCT Pub. Date: Jun. 21, 2007

(65) Prior Publication Data
US 2008/0269341 A1  Oct. 30, 2008

Related U.S. Application Data

(60) Provisional application No. 60/750,004, filed on Dec. 13, 2005.

(51) Int. Cl.
| *A01N 37/18* | (2006.01) |
| *A61K 31/16* | (2006.01) |
| *C07C 233/00* | (2006.01) |
| *C07C 235/00* | (2006.01) |
| *C07C 237/00* | (2006.01) |
| *C07C 239/00* | (2006.01) |

(52) U.S. Cl.
USPC ......................................... 514/627; 564/204

(58) Field of Classification Search
USPC ......................................... 514/627; 564/204
See application file for complete search history.

(56) References Cited

U.S. PATENT DOCUMENTS

2005/0106216 A1  5/2005  Maurer et al.

FOREIGN PATENT DOCUMENTS

| CA | 2442692 | 3/2002 |
| WO | WO 01/07914 | 2/2001 |
| WO | WO0107914 | * 2/2001 |
| WO | WO 2005/084657 A1 | 9/2005 |
| WO | WO 2006002422 A2 * | 1/2006 |

OTHER PUBLICATIONS

Bagga et. al., Nutrition and Cancer, 2002, Lawrence Erlbaum Assoc., vol. 42, No. 2, pp. 180-185.*
Sabichi et. al., Clinical Cancer Research, 2003, American Assoc for Cancer Research, vol. 9, pp. 4606-4613.*
Muskiet et. al., The Journal of Nutrition, 2004, American Society for Nutritional Sciences, vol. 134, pp. 183-186.*
Menard et. al., The Journal of the Cancer Institute, 2001, Oxford University Press, vol. 93, No. 3, pp. 240-241.*
Hope et. al., Inflammation, 1990, Plenum Publishing Corp, vol. 14, No. 5, pp. 543-559.*
International Search Report for International Application PCT/CA2006/002041, mailed by the Canadian Intellectual Property Office as ISA on Apr. 16, 2007.
International Preliminary Report on Patentability for International Application No. PCT/CA2006/002041, mailed by the Canadian Intellectual Property Office as ISA on Jun. 18, 2008.
Gilljam et al., Increased mole fraction of arachidonic acid in bronchial phospholipids in patients with cystic fibrosis. Scand. J. Clin. Lab. Invest. 46: 511-518 (1986).
Sahu et al., Lipid composition of airway secretions from patients with asthma and patients with cystic fibrosis. Am. Rev. Resp. Dis. 115: 233-239 (1977).
Van Handel et al., Micromethod for the direct determination of serum triglycerides. J. Lab. Clin. Med. 50: 152-157 (1957).
Wehrli et al., Visualization and analysis of trabecular bone architecture in the limited spatial resolution regime of in vivo micro-MRI. Noninvasive assessment of trabecular bone architecture and the competence of bone. 153-164 (2001).
Cawood, T.J. et al., Ir. Med. J., 2005, 98 (9):270-273.
Charles, A.G. et al., Cancer Chemother. Pharmacol., 2001, 47(5):444-450.
Conway, S., J. Cyst. Fibros., 2003, 2(4):161-162.
Costa, A. et al., Ann. NY Acad. Sci., 1995, 768:148-62.
Das, U.N., Biotechnol J., 2006, 1(4): 420-439.
Decensi, A. et al., Breast Cancer Research amd Treatment, 1999, 53 :145-151.
Estivill, X. et al., Hum. Mutat., 1997, 10(2) 135-154.
Flohr, F. et al., Eur. J. Endocrinol., 2002, 146(4):531-536.
Folch, J. et al., J. Biol. Chem., 1957, 226(1):497-509.
Freedman, S.D. et al. N. Engl J Med, 2004, 350:560-569.
Freedman, S.D. et al.. PNAS, 1999, 96:13995-14000.
Garaventa, A. et al., Clin. Cancer Res., 2003, 9(6):2032-2039.
Giron, R.M. et al., Med. Clin. (Barc.), 2004, 123(3):81-84.
Giron, R.M. et al., Med. Clin. (Barc.), 2005, 125(9):325-328.
Gronowitz, E. et al., Br. J. Nutr., 2006, 95:1159-1165.
Hecker, T.M. and Aris, R.M., Drugs., 2004, 64(2):133-147.
Lippman, S.M. et al., J. Natl. Cancer Inst., 2001, 93:605-618.
Mollard, R.C. et al., J. Nutr., 2005, 135 :505-512.
Nunes, V. et al., Hum. Genet, 1991, 87(6) : 737-738.
Puduvalli, V.K. et al., Clin. Cancer Res., 1999, 5(8):2230-2235.
Rao, G.N. et al., Breast Cancer Res. Treat., 1998, 48(3):265-271.
Reynolds, C.P. and Lemons, R.S., Hematol. Oncol. Clin. North Am., 2001, 15(5):867-910.
Robinson, R.F. et al., J. Pediatr. Health Care, 2001, 15(6):308-315.
Sun, L. et al., Biosci Biotechnol Biochem, 2004, 68(2):2613-2615.
Turner, C.H., Ann. N.Y. Acad. Sci., 2006, 1068:429-446.

(Continued)

*Primary Examiner* — Sarah Pihonak
(74) *Attorney, Agent, or Firm* — Parker Highlander PLLC

(57) ABSTRACT

The present invention relates to methods for the treatment of a disease or condition associated with lipid imbalance, comprising (a) decreasing arachidonic acid (AA) levels, (b) increasing docosahexaenoic acid (DHA) levels, (c) increasing DHA/AA ratio or (d) any combination of (a)-(c) in a subject using fenretinide. The invention also relates to diagnostic and screening methods based on the determination of lipid levels.

10 Claims, 24 Drawing Sheets

(56) References Cited

OTHER PUBLICATIONS

Ulukaya, E. and Wood, E.J., Cancer Treat Rev., 1999, 25(4):229-235.
Wehrli, F.W. et al., J. Bone Miner. Res., 2001, 16(8):1520-1531.
Guilbault, C. et al. Laboratory Animals, 2005, 39:336-352.
Ponthan, F. et al. Oncology Reports, 2003, 10:1587-1592.
Supplementary European Search Report for European Application No. 06840469.8 (PCT/CA2006/002041), dated Apr. 4, 2011.

* cited by examiner

A. (lungs)

B. (plasma)

A

B

A

B

C

A.

D.

A.

Dunn's Multiple Comparison Test

| Groups | Difference in rank sum | P value | Summary |
|---|---|---|---|
| healthy controls vs DF508/DF508 | 37.45 | P < 0.001 | *** |
| healthy controls vs DF508/other | 39.09 | P < 0.001 | *** |
| healthy controls vs other/ other | 32.04 | P < 0.01 | ** |
| DF508/ DF508 vs DF508/ other | 1.634 | P > 0.05 | ns |
| DF508/ DF508 vs other/ other | -5.413 | P > 0.05 | ns |
| DF508/ other vs other/ other | -7.047 | P > 0.05 | ns |

C.

METHOD FOR CORRECTING A LIPID IMBALANCE IN A SUBJECT

CROSS REFERENCE TO RELATED APPLICATIONS

This application is a U.S. National Phase Application of PCT application No. PCT/CA2006/002041 filed on Dec. 13, 2006 and published in English under PCT Article 21(2) as International Publication No. WO 2007/068116. This application further claims the benefit, under 35 U.S.C. §119(e), of U.S. provisional application No. 60/750,004 filed on Dec. 13, 2005. All of the above applications are incorporated herein by reference in their entirety.

FIELD OF THE INVENTION

The present invention relates to methods, uses and kits for correcting a lipid imbalance, and uses thereof such as for the diagnosis or treatment of disease or condition associated with lipid imbalance. More specifically, the present invention is concerned with correcting levels of docosahexaenoic acid (DHA) and/or arachidonic acid (AA).

BACKGROUND OF THE INVENTION

Essential fatty acid (EFA) and their derivatives are divided into two group; alpha linolenic acid which is the precursor of n-3 polyunsaturated fatty acids (PUFA) and linoleic acid which is the precursor of the n-6 PUFA. Eicosapentaenoic acid (EPA) and docosahexaenoic acid (DHA) are the n-3 PUFA metabolites that have been shown to have potent anti-inflammatory properties acting through transcription factors and gene expression, calcium fluxes, alter membrane fluidity, the regulation and secretion of digestive enzymes and hormones and they also play a role in decreasing susceptibility to inflammatory diseases, such as arthritis and asthma (Das U. N. 2006. Biotechnol J., 1(4):420-439). In contrast arachidonic acid (AA), an n-6 PUFA metabolite, stimulates pro-inflammatory reactions through various prostaglandins and leukotriennes pathways. Gilljam and colleagues studied the role of AA on lung inflammation and infection and discovered a considerable increase in mucus (Gilljam et al., 1986. Scand J Clin Lab Invest. 46(6): 511-8). This increase in inflammation was not secondary to the lung infection but a primary defect attributable to the Cftr gene mutation(s). Epidemiological, clinical, and biochemical studies suggest that the beneficial effects of consuming n-3 PUFA is generally considered to be due to the reduction of AA and its eicosanoid metabolites. DHA and AA are the "yin and yang" of fatty acid metabolism, and disruption of the n-3: n-6 EFA balance results in a number of systemic abnormalities (Das U. N., supra).

Cystic Fibrosis (CF) is characterized by excessive lung inflammation followed by recurrent bacterial infections. At the root of this condition is a defective gene that prevents cells from producing functional Cystic Fibrosis Transmembrane Conductance Regulator proteins (CFTR). The CFTR gene encodes a 1,480 amino acids protein. The most common mutation found in CF patient is deltaF508 (ΔF508); it is a deletion of 3 nucleotides that results in a loss of the amino acid phenylalanine (F) at position 508 of the protein. There are several other mutations which have been associated with CF (Nunes et al., 1991. Hum. Genet. 87(6): 737-8; Estivill X. et al., 1997. Hum. Mutat., 10(2) 135-54). The missing or non-functional CFTR undermine the body's immune system, cause hyperinflammation and cause the body to produce abnormally thick, sticky mucus that clogs the small airways of the lungs and leads to life-threatening lung infections. These thick secretions obstruct other exocrine glands, including the pancreas, preventing digestive enzymes from reaching the intestines to help break down and absorb food. Also, CF patients suffer from a lipid imbalance in the CF-affected organs (Sahu & Lynn (1977) Am. Rev. Respir. Dis. 115:233-239)

Another recently described phenotype associated with CF is reduced bone mineral density, which results in osteopenia and osteoporosis (Gronowitz, E. et al., 2006. Br. J. Nutr. 95:1159-1165; Cawood, T. J. et al., 2005. Ir. Med. J. 98:270-273; Giron, R. M. et al., Med. Clin. (Barc.) 125:325-328; Conway, S. 2003. J. Cyst. Fibros. 2:161-162; Giron, R. M. et al., 2004. Med. Clin. (Barc.) 123:81-84; Flohr, F. et al., 2002. Eur. J. Endocrinol. 146:531-536; Robinson, R. F. et al., 2001. J. Pediatr. Health Care 15:308-315). Osteopenia refers to decreased calcification or density of bones. Osteoporosis literally means "porous bones" and is characterized by low bone density and the structural weakening of bone tissue, which leads to an increased risk of fractures (Turner, C. H. 2006. Ann. N.Y. Acad. Sci. 1068:429-46). Currently, osteoporosis treatment regimen for patients with CF consists of a cocktail of medications including: vitamin D, calcium, vitamin K, sex hormones, anti-resorptive agents such as bisphosphates, anabolic agents such as parathyroid hormone (PTH) and human recombinant growth hormones (HrGH) (Hecker, T. M. and Aris, R. M. 2004. Drugs. 64:133-147; Robinson, R. F., and Nahata, M. C. 2001. J. Pediatr. Health Care. 15:308-315).

There is a need for the development of novel strategies for the diagnosis and treatment of diseases and conditions associated with lipid imbalance.

The present description refers to a number of documents, the content of which is herein incorporated by reference in their entirety.

SUMMARY OF THE INVENTION

The invention relates to methods, uses and kits for correcting a lipid imbalance, and uses thereof such as for the diagnosis or treatment of disease or condition associated with lipid imbalance. More specifically, the present invention is concerned with correcting levels of docosahexaenoic acid (DHA) and/or arachidonic acid (AA).

In an aspect, the present provides a method of (a) decreasing arachidonic acid (AA) levels, (b) increasing docosahexaenoic acid (DHA) levels, c) increasing the DHA/AA ratio, or (d) any combination of (a)-(c) in a subject, said method comprising administering to said subject fenretinide, an analog thereof or a pharmaceutically-acceptable salt thereof.

In an embodiment, the above-mentioned increase or decrease is systemic.

In an embodiment, the above-mentioned subject suffers from a disease or condition associated with a lipid imbalance.

In an embodiment, the above-mentioned subject has (a) a DHA/AA ratio of 0.4 or less, (b) DHA levels of 3.5 ng/μg of phosphate or less, (c) AA levels of 40 ng/μg of phosphate or more or (d) any combination of (a) to (c), prior to said administration.

In an other aspect, the present invention provides a method for assessing bone disease in a subject, said method comprising determining whether (a) DHA level is decreased, (b) AA level is increased, (c) DHA/AA ratio is decreased, or (d) any combination of (a) to (c), in a biological sample of said subject; relative to a corresponding control level or ratio, wherein said increase or decrease is indicative that said subject suffers from bone disease.

In an other aspect, the present invention provides a method for determining whether a subject has an increased risk of developing bone disease, said method comprising determining whether (a) DHA level is decreased, (b) AA level is increased, (c) DHA/AA ratio is decreased, or (d) any combination of (a) to (c), in a biological sample of said subject; relative to a corresponding control level or ratio, wherein said increase or decrease is indicative that said subject has an increased risk of developing bone disease.

In an embodiment, the above-mentioned control level or ratio is selected from a corresponding level or ratio determined in a biological sample from a subject not suffering from bone disease and an established standard level or ratio.

In an embodiment, the above-mentioned method is for prognosticating bone disease and the above-mentioned control level or ratio is determined in a biological sample obtained from said subject at an earlier time.

In an other aspect, the present invention provides a method for identifying a compound for treating or preventing bone disease, comprising determining whether (a) DHA level is decreased, (b) AA level is increased, (c) DHA/AA ratio is decreased, or (d) any combination of (a) to (c), in the presence versus the absence of a test compound,
wherein said increase or decrease is indicative that said test compound can be used for treating or preventing bone disease.

In an other aspect, the present invention provides a method of treating a disease or condition selected from a disease or condition associated with a lipid imbalance, an infectious disease and a bone disease, in a subject, said method comprising:
(i) assessing (a) DHA level, (b) AA level, (c) DHA/AA ratio, or (d) any combination of (a) to (c), in a biological sample obtained from said subject; and
(ii) administering fenretinide to said subject if said (a) DHA level is decreased, (b) AA level is increased, (c) DHA/AA ratio is decreased, or (d) any combination of (a) to (c), relative to a corresponding control level or ratio.

In an embodiment, the above-mentioned control level or ratio is selected from a corresponding level or ratio determined in a biological sample from a subject not suffering from a disease or condition selected from a disease or condition associated with a lipid imbalance, an infectious disease and a bone disease and an established standard level or ratio.

In an embodiment, the above-mentioned method is for prognosticating a disease or condition selected from a disease or condition associated with a lipid imbalance, an infectious disease and a bone disease and the above-mentioned control level or ratio is determined in a biological sample obtained from said subject at an earlier time.

In an other aspect, the present invention provides a use of fenretinide, an analog thereof or a pharmaceutically-acceptable salt thereof for (a) decreasing arachidonic acid (AA) levels, (b) increasing docosahexaenoic acid (DHA) levels, c) increasing the DHA/AA ratio, or (d) any combination of (a)-(c), in a subject.

In an other aspect, the present invention provides a use of fenretinide, an analog thereof or a pharmaceutically-acceptable salt thereof for the preparation of a medicament for (a) decreasing arachidonic acid (AA) levels, (b) increasing docosahexaenoic acid (DHA) levels, c) increasing the DHA/AA ratio, or (d) any combination of (a)-(c), in a subject.

In an other aspect, the present invention provides a composition for (a) decreasing arachidonic acid (AA) levels, (b) increasing docosahexaenoic acid (DHA) levels, c) increasing the DHA/AA ratio, or (d) any combination of (a)-(c) in a subject, said composition comprising:
(a) fenretinide, an analog thereof or a pharmaceutically-acceptable salt thereof; and
(b) a pharmaceutically acceptable carrier.

In an other aspect, the present invention provides a use of the above-mentioned composition for the treatment or prevention of a disease or condition selected from a disease or condition associated with a lipid imbalance, an infectious disease and a bone disease in a subject.

In an other aspect, the present invention provides a use of the above-mentioned composition for the preparation of a medicament for the treatment or prevention of a disease or condition selected from a disease or condition associated with a lipid imbalance, an infectious disease and a bone disease in a subject.

In an other aspect, the present invention provides a package or kit comprising:
(a) the above-mentioned composition; and
(b) instructions for its use for the treatment or prevention of a disease or condition selected from a disease or condition associated with a lipid imbalance, an infectious disease and a bone disease in said subject.

In an embodiment, the above-mentioned subject suffers from an infectious disease. In a further embodiment, the above-mentioned infectious disease is an opportunistic infection. In a further embodiment, the above-mentioned opportunistic infection is a bacterial infection.

In a further embodiment, the above-mentioned bacterial infection is an infection of the respiratory tract and the above-mentioned method or use results in at least a 2-fold, in further embodiments at least a 3-, 4-, 5-, or 10-fold, decrease in bacterial load in the respiratory tract of the subject.

In an other embodiment, the above-mentioned subject suffers from bone disease. In a further embodiment, the above-mentioned bone disease is osteopenia or osteoporosis.

In an embodiment, the above-mentioned treatment results in no or substantially no increase in inflammatory activity (e.g., increase in levels of inflammatory mediators (e.g., cytokines/chemokines); increased recruitment of inflammatory cells into the respiratory tract) in respiratory (e.g., pulmonary, lung, airways) tissue.

In an embodiment, the above-mentioned DHA and AA are phospholipid-associated fractions of DHA and AA.

In an embodiment, the above-mentioned subject is a mammal. In a further embodiment, the above-mentioned mammal is a human.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
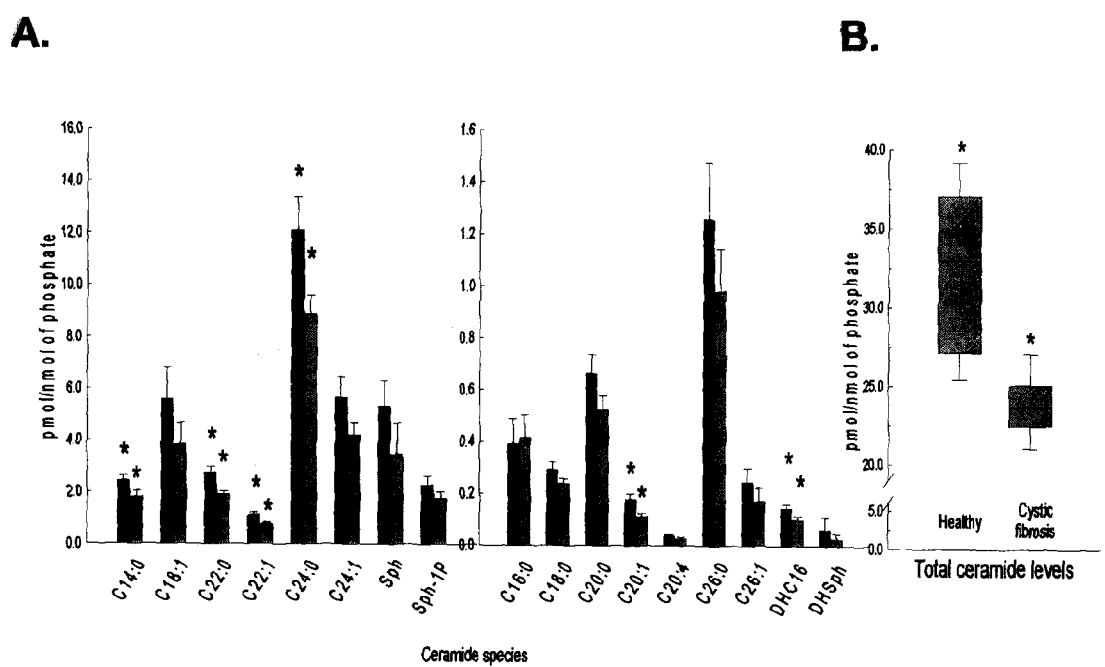
FIG. 1 shows the analysis of 17 sphingolipid metabolites from human samples. Plasma ceramide levels were analysed by HPLC tandem-MS (Bielawski J. et al., 2006. Methods, 39: 82-91) from plasma of healthy controls (n=9, black bars) and CF patients (n=10, grey bars). A. Concentrations of 17 individual ceramides in plasma samples. Plasma samples from CF patients showed significantly (*) lower sphigolipid concentrations than their corresponding healthy controls: C14:0 C14-ceramide (N-Myristoyl-D-erythro-Sphingosine) (P=0.048), C20:1 (Ceramide 20:1) (P=0.017), C22:0 Ceramide (C22:0) (P=0.005), C22:1 Ceramide (C22:1) (P=0.003), C24:0 N-Lignoceroyl-D-erythro-Sphingosine (C24:0) (P=0.033) and Dihydroceramide C16:0 (DHC16:0) (P=0.043). B. Total sum of ceramide concentrations in plasma samples. Seventeen sphingolipid metabolites from human plasma samples were analyzed (14 different ceramides and 3 sphingolipids). Plasma ceramide concentrations were analysed by HPLC tandem-MS using plasma from healthy controls (n=9, black) and cystic fibrosis patients (n=10, grey), as described in Example 1 (Material and methods). B. Total sum of ceramides in plasma samples was calculated for healthy volunteers (n=10) and CF patients (n=10). Samples from CF patients show significantly (*) lower ceramide levels compared with their healthy controls (P=0.0003).

The results presented herein indicate that fenretinide lowers AA levels, increases DHA levels and improves the DHA/AA ratio in several organs from Cftr-KO mice. These overall changes in fatty acid levels lead to major improvements in the bacterial clearance (*P. aeruginosa*) in the lungs of Cftr-deficient mice. The results presented herein also demonstrate that administration of fenritinide is associated with an improvement of bone structure and protection against osteopenia/osteoporosis in Cftr-KO mice.

Accordingly, the present invention provides a method of (a) decreasing arachidonic acid (AA) levels, (b) increasing docosahexaenoic acid (DHA) levels, (c) increasing the DHA/AA ratio, or (d) any combination of (a)-(c) in a subject, said method comprising administering to said subject fenretinide, an analog thereof or a pharmaceutically-acceptable salt thereof.

Fenretinide (all-trans-N-(4-hydroxyphenyl) retinamide), which has CAS registry number 65646-68-6 is a synthetic retinoid. Functional derivatives, analogs or metabolites of fenretinide, such as 4-oxo-N-(4-hydroxyphenyl)retinamide (4-oxo-4-HPR) and N-(4-methoxyphenyl)retinamide (4-MPR) (described in US Patent Application No. 20060264514) can also be used. Fenretinide is particularly suitable for use in the present methods as it is reported to have fewer side-effects compared to naturally-occurring retinoids including vitamin A (Ulukaya and Wood (1999) Cancer Treat Rev. 25:229-35). The safety profile for fenretinide is excellent, as minimal side effects have been noted in a variety of clinical trials using fenretinide on a prophylactic basis (Ulukaya and Wood (1999) Cancer Treat. Rev. 25:229-35). Clinical trials have shown that fenretinide does not induce generalized vascular damage in humans (Reynolds and Lemons (2001) Hematol. Oncol. Clin. North Am. 15:867-910). Fenretinide has also been used to treat subjects (2-21 years of age) with neuroblastoma to define fenretinide pharmacokinetics and maximal tolerated dose in children, and to assess short- and mid-term toxicity in this age range (Garaventa, et al. (2003) Clin. Cancer Res. 9:2032-2039). Fenretinide was given orally once a day in 28-day courses. Liver and renal functions and clinical evaluation were assessed weekly. The side effects that occurred in 15 of the 45 subjects tested were the same as those observed in adult subjects. The side effects were noted to be tolerable and readily reversible within 7 days following discontinuation of the treatment.

Fenretinide has been extensively studied because of its chemo-protective and anti-tumor activities described when used on a variety of malignant cells, including non-small lung cancer, neuroblastoma, Kaposi's sarcoma, breast cancer and glioma (Charles, et al. (2001) Cancer Chemother. Pharmacol. 47:444-450; Garaventa, et al. (2003) Clin. Cancer Res. 9:2032-2039; Lippman, et al. (2001) J. Natl. Cancer Inst. 93:605-618; Ponthan, et al. (2003) Oncol. Rep. 10:1587-1592; Puduvalli, et al. (1999) Clin. Cancer Res. 5:2230-2235; Rao, et al. (1998) Breast Cancer Res. Treat. 48:265-271), and has been approved for clinical trials of cancer patients and is being evaluated in clinical chemoprevention trials in lung, breast, and bladder cancer (Costa, et al. (1995) Ann. NY Acad. Sci. 768:148-62).

An effective amount of an agent (e.g. fenretinide, an analog or metabolite thereof or a pharmaceutically-acceptable salt thereof) or composition disclosed herein is an amount which (a) decreases/reduces AA levels, (b) increases DHA levels, (c) increases or normalizes the DHA/AA ratio or (d) any combination of (a)-(d); an effect which can be determined by monitoring, in a sample, the levels of free AA or DHA or of AA and DHA incorporated into phospholipids. Desirably, the agent decreases the levels of AA in a patient by about 10%, 20%, 30%, 40%, 50%, 60%, 70%, 80%, 90% or 100% as compared to a patient that has not received the agent or increase the levels of DHA by at least about 1.1-fold, 1.2-fold, 1.3-fold, 1.4-fold, 1.5-fold, 1.6-fold, 1.7-fold, 1.8-fold, 1.9-fold, 2-fold, 3 fold, 4-fold, 5-fold or 10-fold. By decreasing the levels of AA and/or increasing the levels of DHA in the patient, an increase of the DHA/AA ratio is achieved. Desirably, the agent increase the DHA/AA by at least about 1.1-fold, 1.2-fold, 1.3-fold, 1.4-fold, 1.5-fold, 1.6-fold, 1.7-fold, 1.8-fold, 1.9-fold, 2-fold, 3 fold, 4-fold, 5-fold or 10-fold. In an embodiment, the DHA/AA ratio is normalized, i.e. the DHA/AA ratio in the patient after treatment is comparable to the DHA/AA ratio in a healthy subject.

Subjects who can particularly benefit from receiving an agent which increases DHA levels and/or decreases AA levels (and consequently increases/normalizes the DHA/AA ratio) are patients suffering from a disease or condition associated with a lipid imbalance or who may be at risk of such a disease or condition, wherein treatment provides a delay or prevention of the disease or condition. A patient with a disease or condition associated with a lipid imbalance is intended to include patients with an excessive accumulation of phospholipid-bound arachidonic acid and/or impairment at the level of DHA incorporated into phospholipids. In one embodiment, the disease or condition is an infectious disease, such as an opportunistic infection (e.g., a bacterial infection) of the respiratory tract including, e.g., *Haemophilus influenzae, Pseudomonas aeruginosa, Streptococcus pneumoniae, Streptococcus pyogenes, Mycobacterium tuberculosis, Candida albicans* or *Aspergillus fumigatus*, and like. In an embodiment, the method of the present invention results in as least a 2-fold, at least a 3-fold, at least a 4-fold, at least a 5-fold, or at least a 10-fold decrease in bacterial load in the respiratory tract of the subject. In another embodiment, the disease or condition is a bone disease, such as osteopenia or osteoporosis.

As used herein, the terms "subject" or "patient" are used interchangeably are used to mean any animal, preferably a mammal, including humans and non-human primates. In an embodiment, the subject suffers from fatty acid or lipid imbalance(s), and more particularly from an excessive accumulation of phospholipid-bound arachidonic acid and/or impairment at the level of DHA incorporated into phospholipids. In an embodiment, the levels of plasmatic DHA or the plasmatic DHA/AA ratio of the patient are about 10% lower than the levels of plasmatic DHA or the plasmatic DHA/AA ratio measured in a healthy subject (i.e. a subject not suffering from a lipid imbalance). Desirably, the levels of plasmatic DHA or the plasmatic DHA/AA ratio in the patient suffering from a lipid imbalance are about 20%, 30%, 40%, 50%, 60%, 70%, 80%, 90% or 100% lower than the levels of plasmatic DHA or the plasmatic DHA/AA ratio measured in a healthy subject. In an embodiment, the levels of AA are at least about 1.1-fold, 1.2-fold, 1.3-fold, 1.4-fold, 1.5-fold, 1.6-fold, 1.7-fold, 1.8-fold, 1.9-fold, 2-fold, 3 fold, 4-fold, 5-fold or 10-fold higher in the patient as compared to the levels measured in a healthy subject.

In an embodiment, the subject who can particularly benefit from receiving an agent is a subject having (a) a DHA/AA ratio of 0.4 or less, (b) DHA levels of 3.5 ng/µg of phosphate or less, (c) AA levels of 40 ng/µg of phosphate or more or (d) any combination of (a) to (c), prior to said administration. In an embodiment, the above-mentioned level or ratio is measured in a biological fluid sample, such as blood, serum or plasma. In a further embodiment, the above-mentioned level or ratio is measured in a plasma sample.

"Disease or condition associated with lipid imbalance" as used herein refers to a disease or condition in which the levels of one or more lipid(s) or in a subject are anomalous or abnormal (i.e. are either higher or lower as compared to the levels of the corresponding lipid(s) in a healthy individual not suffering from the disease or condition). In an embodiment, the lipid imbalance is an imbalance in one or more lipid(s) associated with (or bound to) an essential fatty acid. In a further embodiment, the lipid associated with an essential fatty acid is a phospholipid. In a further embodiment, the essential fatty acid is arachidonic acid (AA) or docosahexaenoic acid (DHA).

"Opportunistic infection" as used herein means invasion by a pathogen of a eukaryotic host in which the conditions are favorable for growth, proliferation, and possible toxin production and subsequent injury to the host. For example, such host can be a subject having a poorly functioning or suppressed immune system caused by an infection (e.g. HIV infection, Respiratory syncytial virus (RSV), etc.) or certain diseases such as cancer, diabetes, Cystic Fibrosis, sickle cell anemia, chronic obstructive lung disease, severe burns, and cirrhosis of the liver. Examples of opportunistic infections include but are not limited to infections with: *Pneumocystis jiroveci* pneumonia, *Candida albicans, Cryptococcus neoformans, Pneumocystis carinii, Escherichia coli Staphylococcus aureus, Staphylococcus epidermidis, Mycobacterium tuberculosis, Streptococcus pyogenes, Streptococcus pneumoniae, Toxoplasma gondii, Cryptosporidium* and *Pseudomonas aeruginosa*.

In an other aspect, the present invention provides a composition for (a) decreasing arachidonic acid (AA) levels, (b) increasing docosahexaenoic acid (DHA) levels, c) increasing the DHA/AA ratio, or (d) any combination of (a)-(c) in a subject, said composition comprising:

(a) fenretinide, an analog thereof or a pharmaceutically-acceptable salt thereof; and (b) a pharmaceutically acceptable carrier.

Agents (e.g. fenretinide) which decrease/reduce arachidonic acid levels and/or increase/normalize DHA levels and the DHA/AA ratio can be prepared for therapeutic use in accordance with the methods disclosed herein by formulating the agents with a pharmaceutically acceptable carrier to obtain a composition (pharmaceutical composition or medicament). In the manufacture of a pharmaceutical formulation, the active agent including the physiologically acceptable salt thereof, is typically admixed with, inter alia, an acceptable carrier. The carrier is acceptable in the sense of being compatible with any other ingredients in the formulation and not be deleterious to the subject. The carrier can be a solid or a liquid, or both, and is preferably formulated with the compound as a unit-dose formulation, for example, a tablet, which can contain from 0.5% to 95% by weight of the active agent. One or more active agents can be incorporated in the formulations of the invention, which can be prepared by any of the well-known techniques of pharmacy consisting essentially of admixing the components, optionally including one or more accessory ingredients. See, e.g., *Remington: The Science and Practice of Pharmacy*, Alfonso R. Gennaro, editor, 20th ed. Lippincott Williams & Wilkins: Philadelphia, Pa., 2000

The formulations of the invention include those suitable for oral, buccal (e.g., sub-lingual), parenteral (e.g., subcutaneous intramuscular, intradermal, or intravenous), and topical (i.e., mucosal surfaces and airway surfaces) administration, although the most suitable route in any given case will depend on the nature and severity of the condition being treated and on the nature of the particular active agent which is being used. Of particular interest are formulations for oral, buccal or topical administration. It is contemplated that the formulations of the instant invention can be used alone or in combination with other therapeutics currently used to treat respiratory tract diseases or cystic fibrosis.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granule containing the active agent, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations suitable for buccal (sub-lingual) administration include lozenges having the active agent in a flavored base, usually sucrose and acacia or tragacanth; and pastilles containing the active agent in an inert base such as gelatin and glycerin or sucrose and acacia.

Formulations for parenteral administration are conveniently sterile aqueous preparations of the active agent, which preparations are preferably isotonic with the blood of the intended recipient. These preparations can be administered by means of subcutaneous, intravenous, intramuscular, or intradermal injection. Such preparations can conveniently be prepared by admixing the compound with water or a glycine buffer and rendering the resulting solution sterile and isotonic with the blood. Formulations for parenteral administration can also be mixed, for example, with vitamin E and/or other suitable food antioxidants and food supplements (such as Peptamen® (Nestlé) or Oxepa® (Abbott laboratories)).

Formulations suitable for topical application (e.g., in the oral passage, nasopharynx, or oropharynx) take the form of an ointment, cream, lotion, paste, gel, spray, aerosol, or oil. Carriers which can be used include vaseline, lanoline, polyethylene glycols, alcohols, transdermal enhancers, and combinations of two or more thereof.

Formulations suitable administration to the trachea or lungs can be in the form of liquid or solid formulations. Formulations are desirably administered as particles of respirable size, e.g., particles of a size sufficiently small to pass through the nose, mouth and larynx upon inhalation and through the bronchi and alveoli of the lungs. In general, respirable particles range from about 0.5 to 10 microns in size. Particles of non-respirable size which are included in the aerosol tend to deposit in the throat and be swallowed, and the quantity of non-respirable particles in the aerosol is thus minimized. For nasal administration, a particle size in the range of 10-500 microns is desirable to ensure retention in the nasal cavity.

Solid particulate compositions containing respirable dry particles of micronized active agent can be prepared by grinding dry compound with a mortar and pestle, and then passing the micronized composition through a 400 mesh screen to break up or separate out large agglomerates. A solid particulate composition containing the active agent can optionally contain a dispersant which serves to facilitate the formation of an aerosol. A suitable dispersant is lactose, which can be blended with the active agent in any suitable ratio, e.g., a 1 to 1 ratio by weight.

Aerosols of solid particles containing the active agent and surfactant can be produced with any solid particulate medicament aerosol generator. Aerosol generators for administering solid particulate medicaments to a subject produce particles which are respirable, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which can be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend containing the active ingredient, a suitable powder diluent, such as lactose, and an optional surfactant. The active ingredient is typically from 0.1 to 100 weight/weight (w/w) of the formulation. A second type of illustrative aerosol generator is a metered dose inhaler. Metered dose inhalers are pressurized aerosol dispensers, typically containing a suspension or solution formulation of the active ingredient in a liquified propellant. During use, these devices discharge the formulation through a valve adapted to deliver a metered volume, typically from 10 to 150 µL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents.

Aerosols of liquid particles containing an active agent of the present invention can be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers contain the active ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, flavorings, volatile oils, buffering agents and emulsifiers and other formulation surfactants.

An aerosol, whether formed from solid or liquid particles, can be produced by an aerosol generator at a rate of from about 10 to 150 liters per minute, more generally from about 30 to 150 liters per minute, and most desirably about 60 liters per minute. Aerosols containing greater amounts of medicament can be administered more rapidly.

An effective amount or dose of any one active agent will vary somewhat from compound to compound, subject to subject, and will depend upon factors such as the condition of the subject and the route of delivery. Such dosages can be determined in accordance with routine pharmacological procedures known to those skilled in the art, particularly in light of the disclosure provided herein and current dosing practices of known active agents.

For example, fenretinide has been used systemically by achieving a plasma level of about 0.1, 2, 3, 5 µM to 10 or 20 µM. For oral dosing, fenretinide is typically used at 50 or 100 to 500 or 1000, 2000 or 3000 mg/m$^2$ body surface area per day. In particular embodiments, 0.1 to 10 µM plasma concentrations are achieved. In an embodiment, the agent (e.g., fenretinide) is administered biweekly.

The invention further provides kits or packages (e.g. commercial packages) comprising the above-mentioned compositions or agents together with instructions for their use for the treatment or prevention of a disease or condition selected from a disease or condition associated with a lipid imbalance, an infectious disease and a bone disease in a subject.

In an other aspect, the present invention provides a method for identifying a compound (e.g. screening method) for treating or preventing bone disease, comprising determining whether (a) DHA level is decreased, (b) AA level is increased, (c) DHA/AA ratio is decreased, or (d) any combination of (a) to (c), in the presence versus the absence of a test compound, wherein said increase or decrease is indicative that said test compound can be used for treating or preventing bone disease.

The screening methods mentioned herein may be employed either with a single test compound or a plurality or library (e.g. a combinatorial library) of test compounds. In the latter case, synergistic effects provided by combinations of compounds may also be identified and characterized. The above-mentioned compounds may be used for prevention and/or treatment of a disease or condition associated with lipid imbalance, or may be used as lead compounds for the development and testing of additional compounds having improved specificity, efficacy and/or pharmacological (e.g. pharmacokinetic) properties. In an embodiment the compound may be a prodrug which is altered into its active form at the appropriate site of action, e.g. in lung tissue. In certain embodiments, one or a plurality of the steps of the screening/testing methods of the invention may be automated.

In accordance with the present invention, the levels of AA or DHA (either free or lipid-bound) can be measured in a biological sample obtained from a subject. In general, typical biological samples include, but are not limited to, sputum, serum, lymphatic fluid, blood, plasma, blood cells (e.g., peripheral blood mononuclear cells), tissue or fine needle biopsy samples, urine, peritoneal fluid, colostrums, breast milk, fetal fluid, tears, and pleural fluid, or cells therefrom. Methods for determining the levels AA and DHA in a biological sample are well known in the art.

In an other aspect, the present invention provides a method of treating a disease or condition selected from a disease or condition associated with a lipid imbalance, an infectious disease and a bone disease, in a subject, said method comprising:
  (i) assessing (a) DHA level, (b) AA level, (c) DHA/AA ratio, or (d) any combination of (a) to (c), in a biological sample obtained from said subject; and
  (ii) administering fenretinide to said subject if said (a) DHA level is decreased, (b) AA level is increased, (c) DHA/AA ratio is decreased, or (d) any combination of (a) to (c), relative to a corresponding control level or ratio.

The control level or ratio can be, for example, a corresponding level or ratio determined in a biological sample from a subject not suffering from a disease or condition selected from a disease or condition associated with a lipid imbalance, an infectious disease and a bone disease. The control level or ratio can also be the level or ratio determined in a biological sample obtained from the same subject but at an earlier time (e.g. when the subject was not afflicted by the disease or condition). The control level or ratio can also correspond to an established standard level or ratio.

The present invention is illustrated in further details by the following non-limiting examples.

EXAMPLES

Example 1

Materials and Methods

Animals. Inbred C57BL/6-Cftr mice breeding pairs, heterozygous (HZ) at the Cftr locus, were used. All babies were genotyped between days 12 and 14 of their life. The animals were kept in cages with sterile corn bedding (Anderson, Bestmonro, La.) and maintained in ventilated racks (Lab Products). Mice were fed with either the NIH-31-modified irradiated mouse diet (Harlan Teklad, Indianapolis, Ind.) or a liquid diet starting at 14 days of age (Peptamen liquid diet; Nestle Canada, Brampton, ON). The liquid diet were freshly prepared every morning and provided in 50-mL centrifuge tubes (Fisher Scientific Ltd, Nepean, ON). Age- and gender-matched C57BL/6-Cftr+/+ (wild-type) mice, (female; n=10, male; n=31) and C57BL/6-Cftr−/− (Cftr-KO) mice (female; n=8, male; n=18) were murine pathogen-, *Helicobacter*- and parasite-free. They were housed (1-4 animals/cage), bred and maintained in a barrier facility unit under specific pathogen-free conditions. Experimental procedures with the mice were conducted in accordance with the Canadian Council on Animal Care guidelines and with the approval of the Animal Care Committee of the McGill University Health Center, Montreal, Quebec, Canada.

Fenretinide Diet Supplementation. Examples 2 to 6: fenretinide (Sigma-Aldrich, Oakville, ON) powder was resuspended in 95% ethanol and subsequently incorporated in the Peptamen liquid diet. It was protected from light and kept at 4° C. before being given to the mice (5 mg/kg per day per mouse). Mock-treated diets were prepared similarly by adding ethanol to the Peptamen diet but omitting the fenretinide supplementation. The diet was given every morning for 28 consecutive days with specific monitoring of the quantity consumed by the mice in each cage. Examples 7 to 12: fenretinide powder was kindly provided by Dr. Robert Smith (NIH; Bethesda, Md., USA). Fenretinide was resuspended in 95% ethanol to make a 2 µg/µL concentration. Approximately 40 µL of this preparation was incorporated into the Peptamen liquid diet (5 mg/kg per day per mouse). The prepared food containing fenretinide was then stored in the dark at 4° C. for no more than 3 hours prior to being administered to the mice. To ensure that the entire drug dose was consumed, the mice were given 10 mL of fenretinide-treated Peptamen, which represents ⅔ of the daily mouse food consumption, in the late afternoon. The remaining 5 mL of Peptamen (without fenretinide) was given the following morning. Mice were treated twice a week for 4 weeks. During the treatment period each mouse was kept in a separate cage (including WT mice) and was monitored to ensure that the entire amount of Peptamen containing the fenretinide or with out was consumed. The diet for the mock-treated control group was prepared and administered similarly to that described above, by adding the same volume of ethanol to the Peptamen diet but omitting the fenretinide supplementation.

*P. aeruginosa* Inoculum Preparation. In order to establish a model of prolonged lung infection, bacteria-impregnated agar beads were freshly prepared the day before each experiment according to established methods (Guilbault, et al. (2005) Laboratory Animals 39:336-352), and stored at 4° C. overnight. Briefly, the bacteria (*P. aeruginosa* strain 508) from an overnight culture were grown for approximately 3 hours in a shaking incubator at 37° C., until it reached a mid-log phase. The log-phase bacteria were concentrated and resuspended in 5 mL of Dulbecco's phosphate-buffered saline (PBS; INVITROGEN™, Mississauga, ON). A 5 mL aliquot of the concentrated bacterial broth was added to 52° C. 1.5% trypticase soy agar (DIFCO®, Detroit, Mich.) (agarose beads free of bacteria were prepared using PBS instead of a bacterial suspension). This mixture was quickly added to 52° C. heavy mineral oil and stirred rapidly, first at room temperature for 6 minutes, followed by ice cooling with continuous stirring for 10 minutes. The oil-agar mixture was centrifuged to sediment the beads. The beads were washed with PBS and their size was verified microscopically and only those preparations containing beads predominantly 100-250 micrometers in diameter were used as inoculum. Inoculum was prepared by diluting the beads suspension to $1 \times 10^6$ CFUs per 50 µl (injection volume).

Mouse Lung Infection. Mice were anaesthetized with a combination of ketamine (7.5 mg/mL) and xylazine (0.5 mg/mL) administered intraperitoneally at a dose of 20 mL/kg of body weight. Once the mouse was successfully anaesthetized, the animal was installed under binoculars (Microscope M650, Wild Leitz, Willowdale, ON) in the vertical position and held on a restraining board by holding the animal by its upper incisor teeth (Guilbault, et al. (2005) supra). The tongue was then gently pulled to the side of the mouth and a 26-G gavage needle was inserted into the mouth and guided through the pharynx gently touching the vocal cords to see the lumen of the trachea; the needle was then introduced into the trachea to reach the lung for the bilateral injection of the 50 microliter inoculum. After inoculation, the animal regained righting reflex within an hour. A final dose of $1 \times 10^6$ *P. aeruginosa* was used for infection using wild-type and Cftr-KO mice. Mice were monitored 3 times daily; the maximum weight loss allowed was 15%. Mice were sacrificed by $CO_2$ overdose.

Bronchoalveolar Lavage. Circulation was flushed by slow intracardiac infusion of divalent cation-free Hank's balanced salt solution (HBSS; INVITROGEN™, Mississauga, ON). The trachea was cannulated with a 22-gauge intravenous catheter placement unit (CRITIKON®, GE Medical Systems, Tampa, Fla.) connected to two 5 mL syringes via a 3-way stopcock with a rotating collar (Namic U.S.A., Glens Falls, N.Y.). The alveoli of infected mice were washed 3 times with 1.4 mL of divalent cation-free HBSS. The volume of bronchoalveolar lavage fluid recovered was approximately 1.2 mL. Alveolar cells were centrifuged and the supernatant was used for CFU count determination before being stored at −20° C., until assayed for cytokine concentrations. Cells were resuspended in 0.5 mL of Dulbecco's Modified Eagle Medium (DMEM; INVITROGEN™) supplemented with 10% fetal bovine serum (FBS; Hyclone, Logan, Utah), diluted in Turk's solution and counted using a hematocytometer. The proportions of macrophages, lymphocytes and PMN were calculated after counting approximately 300 alveolar cells on cytospin preparations stained with DIFF-QUICK® stain (American Scientific Products, McGaw Park, Ill.).

Lung Homogenates. Lungs from infected mice were harvested and homogenized for 60 seconds at high speed (homogenizer PT10135; Brinkmann Instruments Co., Mississauga, ON) in 4 mL of sterile PBS (INVITROGEN™). Serial, 10-fold dilutions of lung homogenates were plated on petri dishes containing TSA. The number of CFU per lung was counted after overnight incubation at 37° C. For cytokine measurements, lung homogenates were centrifuged at 1500×g at 4° C. for 10 minutes; the supernatants were then removed, aliquoted in new tubes and stored at −20° C. until assayed for cytokine concentrations.

Fatty Acid Analysis. Minced tissues isolated from mice were immersed in 1 mM BHA in chloroform and methanol (2:1 vol). For plasma samples (mouse and human), 100 µL of plasma was added to 1 mL of BHA. Lipids were then extracted from all samples according to standard methods (Folch, et al. (1957) J. Biol. Chem. 226:497-509). Identification of phospholipids was carried out by thin-layer chromatography extraction (Van Handel & Zilversmit (1957) J. Lab. Clin. Med. 50:152-157). Also, fractionated lipids were dried and resuspended in heptane:methanol:sulfuric acid (5:1:1) for free fatty acid extraction. Diazomethane was used to esterify the fatty acids released and the esters were identified by GC/MS (Hewlett Packard 5880A, WCOT capillary column (Supelco-10, 35 m×0.5 mm, 1 µm thick)) using commercial standards (Sigma-Aldrich).

Ceramide/Sphingolipids analysis. The concentration of ceramide in the (lung, liver, ileum, pancreas homogenates) and plasma from mice and humans were determined by ELISA[39;40] on separated lipids samples by thin layer chromatography, as described above. The phospholipids from the dry silica were resuspended in ethanol and used to coat Nunc plates specific for lipid binding. Plates were then washed, incubated with blocking buffer for 1 hr at 37° C. (PBS, 0.1% Tween 20, and 1% bovine serum albumin (BSA; Sigma, Oakville, ON), and subsequently incubated with murine anti-ceramide IgM (Sigma-Aldrich) antibody (Ab) for 1 hr at 37° C. The plates were washed again and then incubated with peroxidase-conjugated anti-mouse IgM Ab for 1 hr at 37° C. Finally, the plates were incubated with the peroxidase substrate (TMB; Roche, Laval, QC). The intensity of the colorimetric reaction was determined by spectrophotometry at 405 nm. The levels of ceramide were calculated with reference to a standard curve using ceramide (Sigma-Aldrich). Phosphate levels were assessed, as previously described, by the PiBlue™ Phosphate assay (Boehringer Ingelheim, Chuao, Caracas), according to the manufacturer's instructions.

µ-CT. Mice were sacrificed by $CO_2$ and exsanguinated by cardiac puncture. Femurs, tibiae and vertebrae were extracted, stripped of soft tissue and fixed in 4% paraformaldehyde overnight. Micro Computed Tomography (µCT) was performed on the left femur after overnight fixation. The distal metaphysis was scanned with a Skyscan 1072 µCT instrument (Skyscan, Antwerp, Belgium). Image acquisition was performed at 100 kV and 98 µA, with a 0.9° rotation between frames. The two-dimensional images were used to generate three-dimensional reconstructions to obtain quantitative data using the 3D Creator software supplied with the instrument (ANT 3D Creator software, Skyscan, Antwerp, Belgium).

Histological analysis. Mice were given an intra-peritoneal injection of 30 mg/kg calcein at 7 days and 2 days prior to sacrifice to label actively mineralizing surfaces. After overnight fixation in 4% paraformaldehyde and rinsing in phosphate buffered saline (PBS), right femurs and tibiae were embedded in polymethylmethacrylate (MMA) or a mixture of 50% MMA and 50% glycolmethacrylate (GMA). Serial 4- to 6-μm sections were cut on a modified Leica RM 2155 rotary microtome (Leica Microsystems, Richmond Hill, Ontario, Canada). MMA-embedded tissues were stained with von Kossa and toluidine blue, while 4 μm MMA-GMA sections were stained with tartrate-resistant acidic phosphatase (TRAP) and alkaline phosphate (ALP) activity. Images were captured using a Leica DMR microscope (Leica Microsystems) equipped with a Retiga 1300 camera (Qimaging, Burnaby, British Columbia, Canada). The left femur and tibia and the lumbar vertebrae were decalcified with 4% EDTA for paraffin embedding after 14 days. Serial 5 μm sections were cut and stained with hematoxylin and esosin (H&E). Osteoblasts were defined as a single-nucleated, rod shaped cells and were identified along the surface of the trabecular lamellae. Osteoclasts were defined as multi-nucleated cells that are much larger then osteoblasts and display typical macrophage morphology.

Cytokine/chemokine measurements. The levels of 10 cytokines/chemokines (IL-1β, IL-6, IL-7, IL-9, IL-10, IL-15, IL-17, G-CSF (granulocyte colony-stimulating factor), MIP-1a (macrophage inflammatory protein 1 alpha), and N51/KC (cytokine-induced neutrophil chemoattractant), were assessed in lung homogenates prepared from infected animals with the Mouse Cytokine/Chemokine LINCOplex kit (Linco Research, Inc, St-Charles, Mo.) using Luminex™ technology and assayed with the Luminex100LS™ system by Linco Research, Inc. The cytokine detection limit for this assay was 3.2 pg/ml.

Statistical Analyses. Examples 2 to 6: data were analyzed using Sigma Stat V3.1 software (SPSS Inc, Chicago, Ill.). Statistically significant differences between means and medians of studied groups were evaluated using Student's t-test and nonparametric Mann-Whitney U test, respectively. One-way ANOVA and Kruskal-Wallis ANOVA on ranks, combined with the appropriate pair wise multiple comparison procedures were used to evaluate the differences between multiple groups. Significance was set at a two-tailed p value of ≤0.05. Example 7 to 13: data was analyzed using GraphPad Prism Version 4.03 software (GraphPad Software, San Diego, Calif., United States). All data was analyzed by parametric one way analysis of variance (ANOVA) followed by Bonferroni multiple comparison test. Significance was set at a two-tailed P value of ≤0.05.

CF patients. For the preliminary analysis of ceramide levels, plasma samples were collected from patients with cystic fibrosis, enrolled in a CF clinic (Montreal Chest Institute Research Center, McGill University Health Center). The patients were recruited having a broad range of CFTR genotypes and were between 18 and 62 years old. No patient was excluded because of race, sex or ethnic background.

Healthy volunteers. Subjects were recruited at the McGill University Health Centre associated hospitals. Inclusion criteria for the study included males and females aged-matched with CF subjects and having no life threatening episodes of any disease within the previous 6 months. Exclusion criteria included evidence of alcohol or drug abuse, any clinically significant disease, immunotherapy treatments within the previous 6 months and the use of any drugs regulating lipid metabolism in the last 6 months. The study was approved by the Research Ethics Board & Office of Clinical Contracts of the Montreal Chest Institute.

Data Collection. Each participant was assigned an arbitrary number which was kept from those processing and analyzing the samples to prevent bias in interpretation of the results. CF patients and healthy volunteers were asked for their height and weight to calculate their body-mass index. CF patients also disclosed their chart information regarding pulmonary and infection status.

Blood preparation. Three (3) mL of blood were taken from each patient in BD Vacutainer® spray-coated K2EDTA tubes (BD, Franklin Lakes, N.J., USA) for plasma and DNA extractions. Another two milliliters in BD Vacutainer® SST™ Tubes (BD) were taken for serum collection. Tubes were spun at 1100 rpm for 10 minutes at 4° C. For fatty acid analysis, 100 μL of plasma was added to 1 mL of butylated hydroxylanisole solution (100 mM BHA in 2:1 chloroform/methanol) and stored at −80° C. Serum and plasma were aliquoted and stored in −80° C. for further analysis.

Example 2

Ceramide Levels in Plasma of CF Patients and Healthy Volunteers (Mass Spectroscopy Analysis)

Applicant first sought to determine if people affected by CF showed different levels of ceramides in their blood compared to a control group. The characteristics of the human subjects (healthy and CF) are provided in Table 1.

TABLE 1

Characteristics of human subjects; Mass Spectroscopy analysis

|  | Healthy volunteers | Cystic fibrosis patients |
|---|---|---|
| N | 10 | 10 |
| Age | 34.7 ± 3.7 | 37.2 ± 4.2 |
| Weight (Kg) | 70.1 ± 4.3 | 58.5 ± 3.0 |
| Height (cm) | 166.2 ± 3.4 | 166.7 ± 3.4 |
| BMI | 25.4 ± 1.3 | 21.0 ± 1.0 |
| Genotypes | | ΔF508/ΔF508 |
| | | ΔF508/ΔF508 |
| | | ΔF508/ΔF508 |
| | | ΔF508/R334w |
| | | ΔF508/unknown |
| | | ΔF508/unknown |
| | | ΔF508/unknown |
| | | ΔF508/unknown |
| | | 621 + 1G > T/L206W |
| | | unknown/unknown |

The plasma of CF patients and healthy volunteers was tested for ceramide levels and the results obtained demonstrated that disparities exist in specific ceramide species among these two groups. As shown in FIG. 1A, C14:0 (P=0.048), C20:1 (P=0.017), C22:0 (P=0.005), C22:1 (P=0.003), C24:0 (P=0.033) and DH-C16:0 (P=0.043) showed a statistically significant reduction in CF patients compared to their sex- and age-matched healthy controls. All the other varieties of ceramide analyzed were not statistically different between the two groups (P values ranging from 0.133 to 0.732). The overall difference in cumulative ceramide levels between CF patients and healthy controls was highly significant (P=0.0003), as demonstrated by the sum of the analyzed species in FIG. 1B.

Example 3

Analysis of Ceramide Levels in Cftr-KO Mice

Ceramide levels in Cftr-KO mice (murine model of cystic fibrosis) were analyzed. Cftr-KO mice have a complete deletion of the CFTR gene and spontaneously develop lung disease over a certain period of time. An alternative, more affordable method to the Mass Spectroscopy (MS) technique was developed and used to analyze the ceramide levels. The efficacy of an ELISA assay using a monoclonal antibody that recognizes many species of ceramide was assessed by comparing the results obtained with those obtained by mass spectroscopy. To decrease the possibility that the monoclonal antibody (mAb) recognizes other lipids than ceramide derivatives, the plasma samples were prepared by separating the phospholipids by thin layer chromatography (TLC) and then processed the separated sample by ELISA (see Example 1).

Thirty (30) samples were arbitrarily selected to undergo the analysis by both methods. Linear regression analysis showed that the ELISA detected the total ceramide levels similarly to the MS method (Table 2, P=0.002). The analysis was then performed in mice lung and plasma samples using the ELISA assay to measure the ceramide levels in wild-type and Cftr-KO mice.

TABLE 2

Linear regression analysis; MS vs. ELISA ceramide levels detection

| N | $R^2$ | F | P value |
|---|-------|----|---------|
| 30 | 0.293 | 11.6 | 0.002 |

Figure 2:
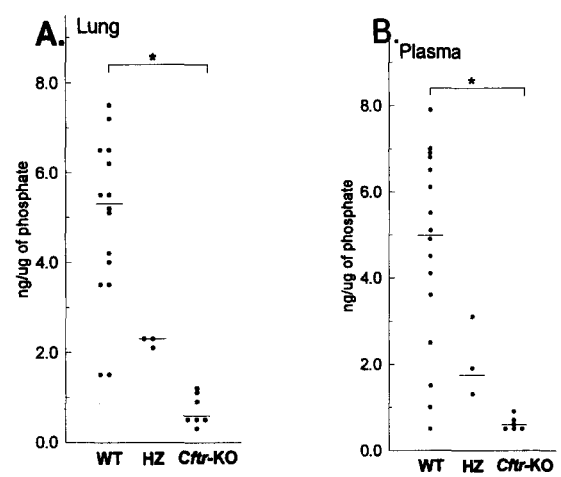
FIG. 2 shows an analysis of ceramides levels in uninfected wild-type and Cftr-KO mice. Ceramides levels in the lungs (FIG. 2A, left panel) and plasma (FIG. 2B, right panel) of wild-type (WT, n=33), heterozygous (HZ, n=6) and Cftr-KO (n=17) mice were determined by ELISA (see Example 1).

The basal levels of ceramide found in the lung and plasma samples of Cftr-KO mice, mice heterozygous for the Cftr gene (HZ) and their WT controls was measured. As seen in FIG. 2, uninfected mice with diverse combinations of the functional or aberrant CFTR gene have significantly different levels of endogenous ceramide in their lung tissue (panel A, P≤0.001) and plasma (panel B, P=0.002). There were remarkable differences (±10-fold) in the median ceramide levels between the Cftr-KO and WT mice, for both lung and plasma samples. The levels of ceramide in Cftr-KO mice were barely detectable. Interestingly, HZ mice, which possess one normal and one ablated allele of Cftr gene, have 2.3-fold less ceramide levels in the lungs and 2.6-fold less ceramide levels in the plasma compared to their WT counterparts. These interesting findings further support the existence of a relationship between the Cftr genotype and the levels of ceramide detected in the lungs of these mice. No correlation was found between the ceramide levels in the lungs and the weight of the mice (WT; P=0.061, Cftr-KO; P=0.687), nor between the ceramide levels in the lungs and the age of the mice (WT; P=0.251, Cftr-KO; P=0.187).

The effect of fenritinide administration on ceramide levels in these mice was then studied. Fenretinide treatment caused an increase in the levels of ceramide, as clearly shown in Table 3. WT mice that were treated with fenretinide showed the smallest increase, with a 1.4-fold (lung) and 1.6-fold (plasma) increase in their ceramide levels compared to their untreated WT counterparts. HZ mice showed an intermediate effect with a 2.1-fold (lung) and 2.7-fold (plasma) increase compared to their HZ untreated counterparts. Cftr-KO mice had the most impressive impact demonstrating 7.0-fold (lung) and 6.9-fold (plasma) increase in average levels of ceramide as compared to their untreated Cftr-KO counterparts. These augmentations in ceramide levels caused by fenretinide in the Cftr-KO lead to the vanishing of the difference that existed (as depicted in FIG. 2) between the Cftr-KO mice and the WT mice at the basal levels, in both the lung and plasma samples (data not shown), bringing the ceramide levels both groups of mice to similar levels.

TABLE 3

Ceramide levels induction by fenretinide in uninfected mice

| Cftr genotype | Fold-increase (FEN-treated over CTRL*) | |
|---|---|---|
| | Lung | Plasma |
| WT | 1.4 (n = 10) | 1.6 (n = 12) |
| HZ | 2.1 (n = 3) | 2.7 (n = 3) |
| Cftr-KO | 7.0 (n = 3) | 6.9 (n = 3) |

*CTRL groups include untreated and mock-treated samples

Figure 3:
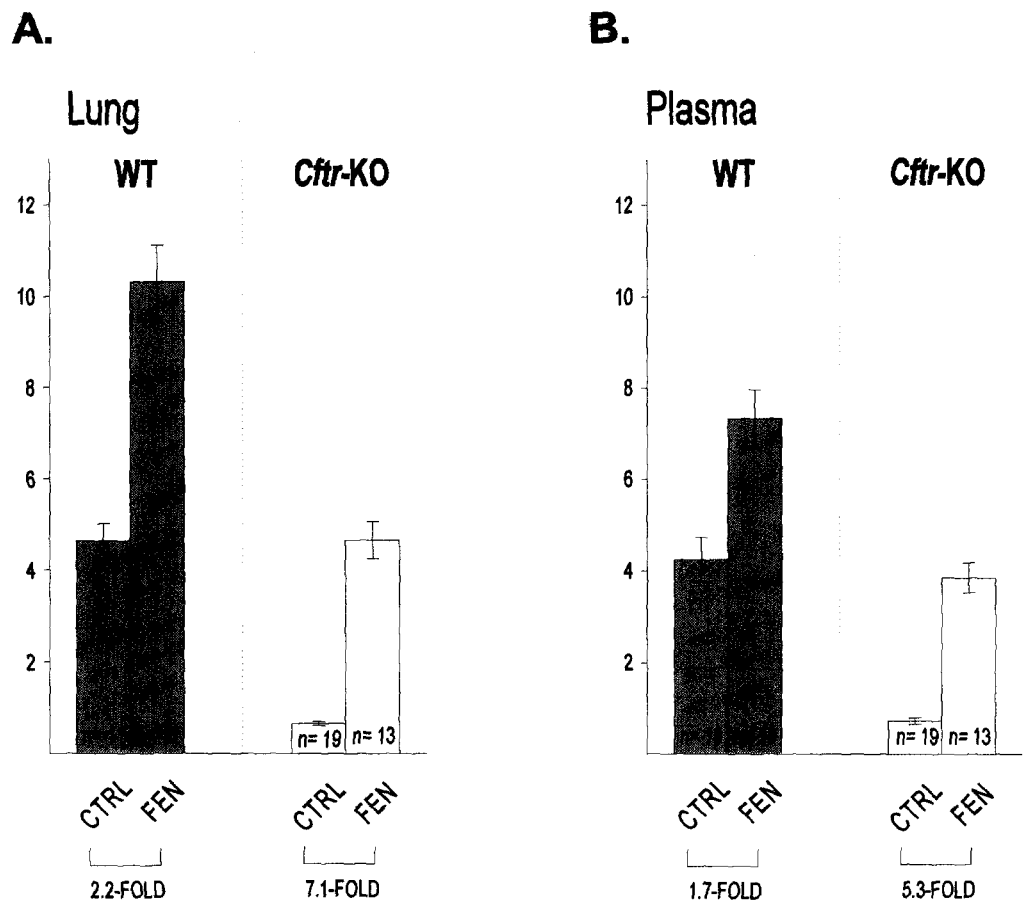
FIG. 3 shows an analysis of ceramide levels in P. aeruginosa infected wild-type (grey bars) and Cftr-KO (white bars) mice. Ceramide levels in the lungs (FIG. 3A, left panel) and plasma (FIG. 3B, right panel) were determined by ELISA (see Example 1). CTRL=mock-treated; FEN=treated with fenretinide.

Infection with *P. aeruginosa* did not per se affect the ceramide levels detected in the lungs when compared to the levels found in uninfected mice for both WT (p=0.715) and Cftr-KO (p=0.630) animals (data not shown). We then assessed the ceramide levels in infected mice that were either not treated/mock-treated (EtOH) or treated with fenretinide. In *P. aeruginosa*-infected mice (FIG. 3), we observed significantly (p≤0.001) lower levels of ceramide in the lungs (FIG. 3A) and plasma samples (FIG. 3B) of Cftr-KO mice (white bars) as compared to WT infected controls (grey bars) in both mock-treated (CTRL) and fenretinide-treated (FEN) mice. Moreover, when mice were treated with fenretinide, an increase in the levels of ceramide was observed in both WT and Cftr-KO mice, when compared to their respective mock-treated control groups. An approximately 7-fold increase in ceramide levels was measured in the fenretinide-treated Cftr-KO mice compared to their mock-treated Cftr-KO controls. As for the WT mice, fenretinide treatment also induced an increase in ceramide levels as compared to their untreated WT counterparts, but to a smaller magnitude (approx. 2-fold) compared to the Cftr-KO. Interestingly, the ceramide levels observed in the fenretinide-treated Cftr-KO reached similar levels as those observed in the mock-treated WT mice. Overall, these results indicate that Cftr-KO mice have lower basal levels of ceramide in the lungs compared to their wild-type controls prior and during *P. aeruginosa* infection. Unexpectedly, treatment with fenretinide was able to considerably increase the levels of ceramide in the lungs and plasma tissues in the Cftr-KO mice.

A statistically significant weight difference between the Cftr-KO (n=14) and wild-type (n=17) mice was also observed as determined by mean weight loss percentage at day 2 and day 3 post-infection (Table 4).

TABLE 4

| Days post-infection | Mean weight loss (% of initial weight) | | | | |
|---|---|---|---|---|---|
| | Wild-type | ±SEM | Cftr-KO | ±SEM | P value |
| 1 | −4.5 | 0.4 | −4.7 | 0.9 | 0.799 |
| 2 | −10.1 | 0.6 | −13.5 | 1.5 | 0.030* |
| 3 | −11.2 | 0.9 | −16.2 | 1.9 | 0.016* |

SEM, standard error of the mean.
*Statistically significant differences between the wild-type and the Cftr-KO mice (P ≤ 0.05).

Carefully monitoring was conducted to determine whether supplementation of the diet with fenretinide might affect the mean weight loss and no significant difference in the percentage between the fenretinide-treated and the mock-treated control groups was observed at any of the days post-infection (P≤0.05 for day 1 to day 3 post-infection; Table 5).

TABLE 5

| Days post-infection (P value) | Mean weight loss (% of initial weight) | | | |
|---|---|---|---|---|
| | Wild-type | | Cftr-KO | |
| | CTRL n = 6 | FEN n = 11 | CTRL n = 6 | FEN n = 8 |
| 1 (0.598) | −3.9 ± 0.8 | −4.8 ± 0.4 | −5.7 ± 1.7 | −4.0 ± 1.1 |
| 2 (0.179) | −10.6 ± 1.3 | −9.9 ± 0.5 | −14.2 ± 3.2 | −12.9 ± 0.9 |
| 3 (0.114) | −11.2 ± 1.3 | −11.1 ± 1.2 | −17.2 ± 3.7 | −15.3 ± 1.8 |

Data are presented as the mean weight loss ± SEM.
CTRL: untreated or mock-treated;
FEN: fenretinide-treated.

Example 4

Inflammatory Cells in the Lungs of Wild-Type and Cftr-KO Mice Following Administration of Fenretinide The number of alveolar cells from the bronchoalveolar lavage fluid were evaluated in both Cftr-KO (n=20) and wild-type (n=25) mice 3 days after infection with $1 \times 10^6$ *P. aeruginosa* embedded in agar beads. The treatment with fenretinide had no effect on the cells recruited into the lungs of infected mice compared to the mock-treated mice at day 3 post-infection. Specifically, no significant difference in the mean total number of alveolar cells in the lungs was found between the mock-treated Cftr-KO mice ($1.2 \times 10^6 \pm 1.6 \times 10^6$) and the fenretinide-treated Cftr-KO mice ($1.1 \times 10^6 \pm 1.3 \times 10^6$) (p=0.530). Similarly, no significant difference in the mean total number of alveolar cells in the lungs was observed between the mock-treated wild-type mice ($1.0 \times 10^6 \pm 1.6 \times 10^6$) and the fenretinide-treated wild-type mice ($1.2 \times 10^6 \pm 1.0 \times 10^6$) (p=0.280). When the amount of different types of inflammatory cells found in the lungs of fenretinide-treated and mock-treated infected mice were quantified and compared, no significant differences between the groups were found. This applied to all different types of inflammatory cells studied and for both wild-type and Cftr-KO mice (neutrophils, p=0.143; monocytes, p=0.223; lymphocytes, p=0.400). In summary, fenretinide treatment does not influence the amounts of different types of inflammatory cells in the mouse model of *P. aeruginosa*-lung infection employed on day 3 post-infection.

Lung homogenates from WT and Cftr-KO mice were also tested to determine the level of 10 cytokines to evaluate the potential inflammatory effects of diet supplementation with fenretinide. Statistically lower IL-17 (2.9-fold decrease; p=0.049) levels were detected in Cftr-KO mice when they were treated with fenretinide compared to the Cftr-KO controls. A trend towards decreased levels of IL-1β, IL-9, KC and MIP-1a was also observed in the fenretinide-treated Cftr-KO mice compared to their mock-treated control group, although these differences did not attain statistical significance (data not shown): IL-6, G-CSF, IL-15, IL-10 and IL-7 levels were also analyzed and were not affected by the fenretinide treatment, at least not at the time point tested (data not shown). In the WT mice, no difference between fenretinide-treated and untreated mice was observed, for all the cytokines tested.

Example 5

Figure 4:
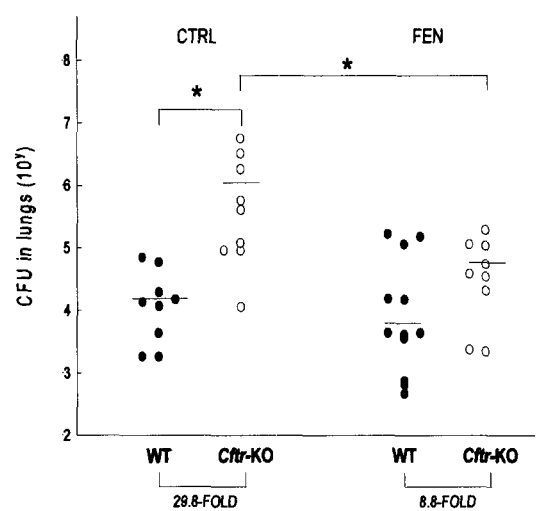
FIG. 4 shows the bacterial load in the lungs of P. aeruginosa-infected wild-type and Cftr-KO mice. Colony Forming Units (CFUs) from the lungs of P. aeruginosa-infected wild-type (WT, black circles) and Cftr-KO (white circles) mice that were untreated/mock-treated (CTRL) or treated with fenretinide (FEN) was determined 3 days post-infection.

Effect of Fenretinide on the Bacterial Load in the Lungs of Wild-Type and Cftr-KO Mice It was also assessed whether the treatment with fenretinide affects the bacterial load in the lungs of the Cftr-KO and wild-type mice at day 3 post-infection with *P. aeruginosa* (FIG. 4). The untreated Cftr-KO mice had significantly higher median colony-forming unit (CFU) counts in the lungs compared to their wild-type counterparts (p=0.004). There was approximately a 30-fold difference in the bacterial load in the lungs between Cftr-KO and wild-type mice. Unexpectedly, the treatment regiment with fenretinide dramatically decreased (about 10-fold) the median number of bacteria that was found in the treated Cftr-KO compared to the untreated Cftr-KO mice (untreated Cftr-KO=$4.0 \times 10^5$ CFU/lung compared to fenretinide treated Cftr-KO=$3.8 \times 10^4$ CFU/lung, p=0.004). Not only was a decrease in the bacterial burden of the Cftr-KO observed, but the CFU counts dropped down to the levels of the wild-type (no statistically significant difference found between fenretinide-treated Cftr-KO and wild-type groups of mice, p=0.086). Fenretinide had no significant effect on the median number of bacteria found in the lungs of the wild-type mice compared to their wild-type untreated *P. aeruginosa*-infected controls (p=0.240).

Example 6

Effect of Fenretinide on the DHA/AA Ratio

DHA and AA levels were assessed in different organs of untreated, mock-treated or fenretinide-treated mice uninfected or lung-infected with *P. aeruginosa*.

Figure 5:
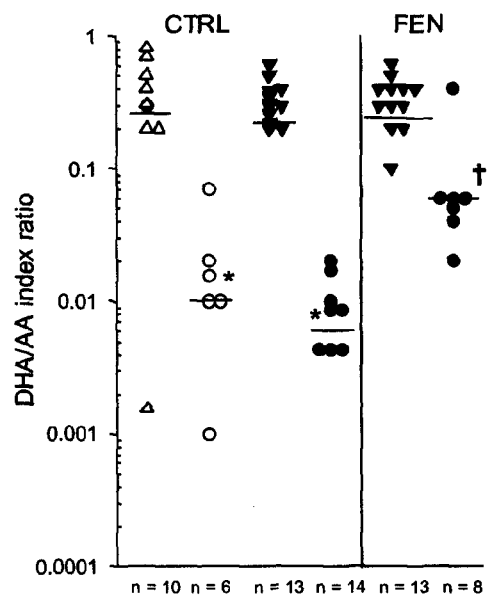
FIG. 5 shows DHA/AA index ratio observed in the lungs and plasma. DHA/AA index ratio in the lungs (FIG. 5A) and in the plasma (FIG. 5B) were assessed in wild-type (triangles) and Cftr-KO (circles) mice which were not-infected (open) or P. aeruginosa-infected at 3 days post-infection (closed) and that were either not treated or mock-treated (CTRL) or treated with fenretinide (FEN).
Figure 5:
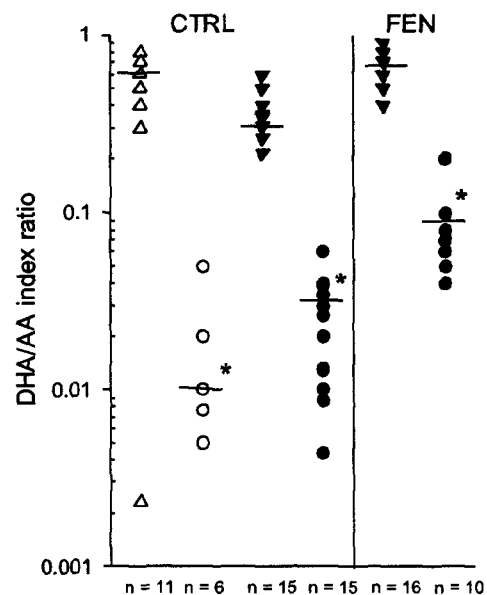

Unexpectedly, in the lungs and in the plasma of untreated mice, a lower median (p≤0.001) index ratio of DHA/AA was observed in the Cftr-KO mice compared to their wild-type controls (FIGS. 5A and 5B, CTRL panels, white symbols). Also, when the mice were infected with *P. aeruginosa* in the lungs (FIGS. 5A and 5B, CTRL panels, black symbols), a significantly lower (*) median DHA/AA index ratio was observed in the lungs of Cftr-KO mice compared to wild-type infected controls in both the lungs (FIG. 5A, p≤0.001) and plasma (FIG. 5B, p≤0.001). When the mice were treated with fenretinide, an increase in the DHA/AA median index ratio was observed in the lungs and plasma of infected Cftr-KO mice compared to the Cftr-KO untreated control mice (FIG. 5). However, this difference reached statistical significance only in the lungs (†) because the plasma samples showed higher intragroup variability. As for the wild-type mice, the fenretinide treatment had no effect on the DHA/AA median index ratio in both lungs and plasma compared to their untreated wild-type control mice. Since fenretinide treatment had an effect on the DHA/AA ratio in the Cftr-KO mice but not in the wild-type mice, the increase observed in the treated Cftr-KO mice reached the level at which a difference between the infected wild-type and Cftr-KO fenretinide-treated mice (FIG. 5A, FEN panel) compared to the untreated wild-type and Cftr-KO mice (FIG. 5A, CTRL panel) could no longer be observed. The fenretinide treatment lowered the difference in the median index ratio between the wild-type and Cftr-KO by approximately 10-fold (untreated wild-type/Cftr-KO=67-fold versus FEN-treated wild-type/Cftr-KO=7-fold). These results clearly demonstrated that fenretinide treatment had a very profound impact on the DHA/AA ratio. This treatment protocol was able to normalize the abnormal DHA/AA ratio observed in both uninfected and infected Cftr-KO mice to ratios similar to those observed in uninfected and infected wild-type mice.

Figure 6:
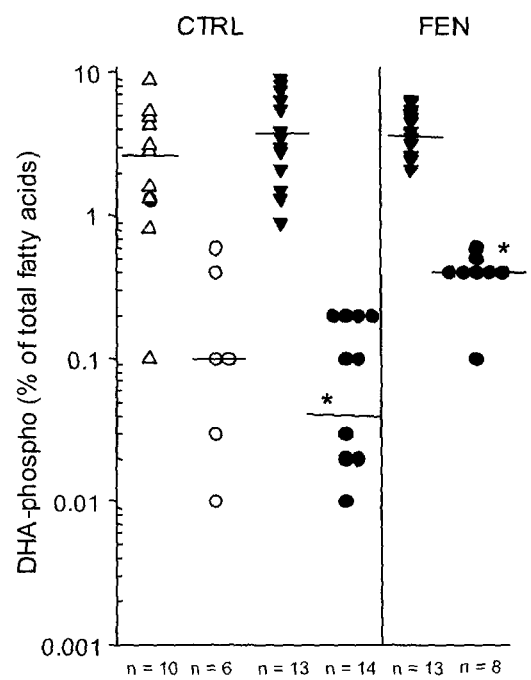
FIG. 6 shows DHA incorporated in phospholipids expressed as percentage of total fatty acids in the lungs and plasma. DHA levels in the lungs (FIG. 6A) and in the plasma (FIG. 6B) were assessed in wild-type (triangles) and Cftr-KO (circles) mice which were not infected (open) or P. aeruginosa-infected (closed) at 3 days post-infection and that were either not treated or mock-treated (CTRL) or treated with fenretinide (FEN).
Figure 6:
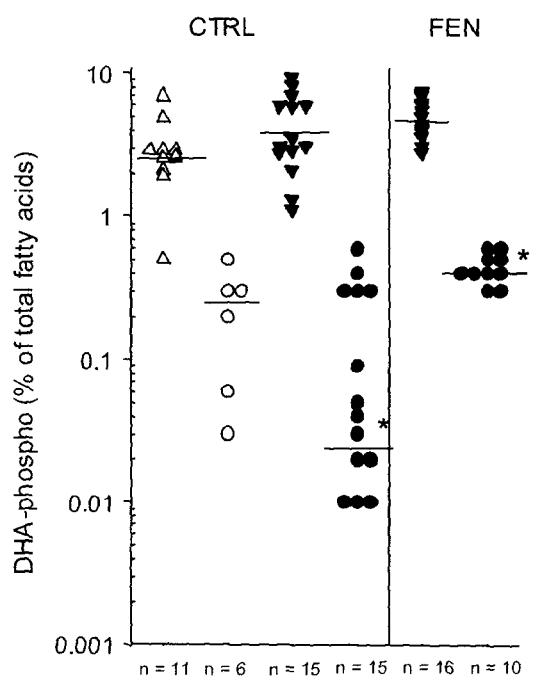

DHA levels in the lungs and in the plasma were assessed in wild-type and Cftr-KO mice which were not-infected or *P. aeruginosa*-infected at 3 days post-infection. The mice were either not treated or mock-treated (CTRL) or treated with fenretinide (FEN). The levels of DHA incorporated in phospholipids were evaluated and the data were expressed as percentile of total fatty acids (FIG. 6). Lung (p≤0.001) and plasma (p≤0.001) samples were statistically different between the groups of mice tested. The Cftr-KO *P. aeruginosa* infected mice showed lower median (*) DHA levels compared to their wild-type infected controls in both the lungs and the plasma (FIG. 6, CTRL panels). The fenretinide-treated mice showed no difference in the median DHA levels in the lungs and plasma of infected Cftr-KO mice compared to the Cftr-KO untreated control mice. Similarly, the wild-type treated with fenretinide showed no difference in the median DHA level in both lungs and plasma compared to their untreated wild-type control mice.

Figure 7:
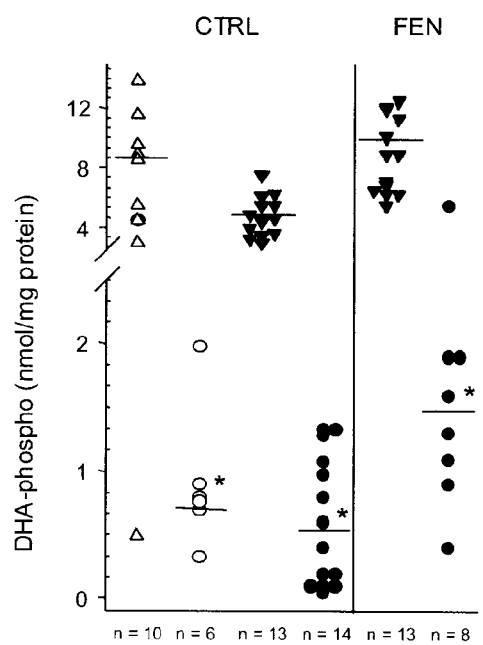
FIG. 7 shows the concentration of DHA incorporated in phospholipids in the lungs and plasma. DHA levels in the lungs (FIG. 7A) and in the plasma (FIG. 7B) were assessed in wild-type (triangles) and Cftr-KO (circles) mice which were not-infected (open) or P. aeruginosa-infected at 3 days post-infection (closed) and that were either not treated or mock-treated (CTRL) or treated with fenretinide (FEN).
Figure 7:
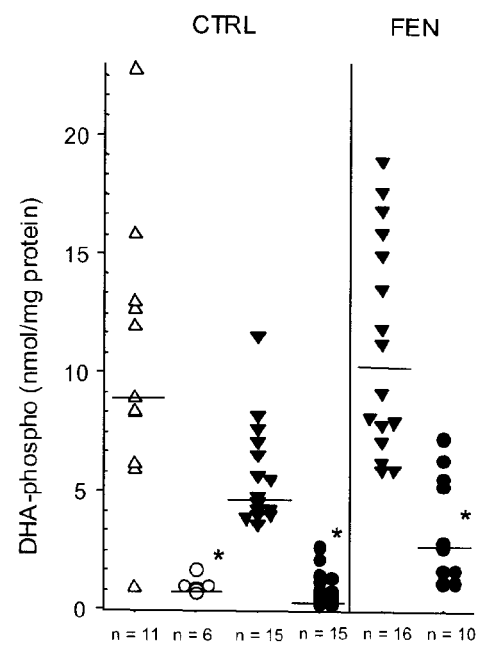

The specific concentration of DHA incorporated in phospholipids was also evaluated and expressed in nmol/mg of protein (FIG. 7). The Cftr-KO uninfected mice showed lower median (*) DHA concentration levels compared to their wild-type uninfected controls in both the lungs and the plasma (FIG. 7, CTRL panels). Similarly, the Cftr-KO *P. aeruginosa*-infected mice showed lower median (*) DHA levels compared to their wild-type infected controls in both the lungs and the plasma (FIG. 7, CTRL panels). The fenretinide-treated Cftr-KO infected mice showed lower median (*) DHA levels compared to their wild-type infected controls in both the lungs and the plasma (FIG. 7, CTRL panels). These results indicate that the fenretinide-mediated increase observed in the DHA/AA ratio was not due to the levels of DHA incorporated in phospholipids.

Figure 8:
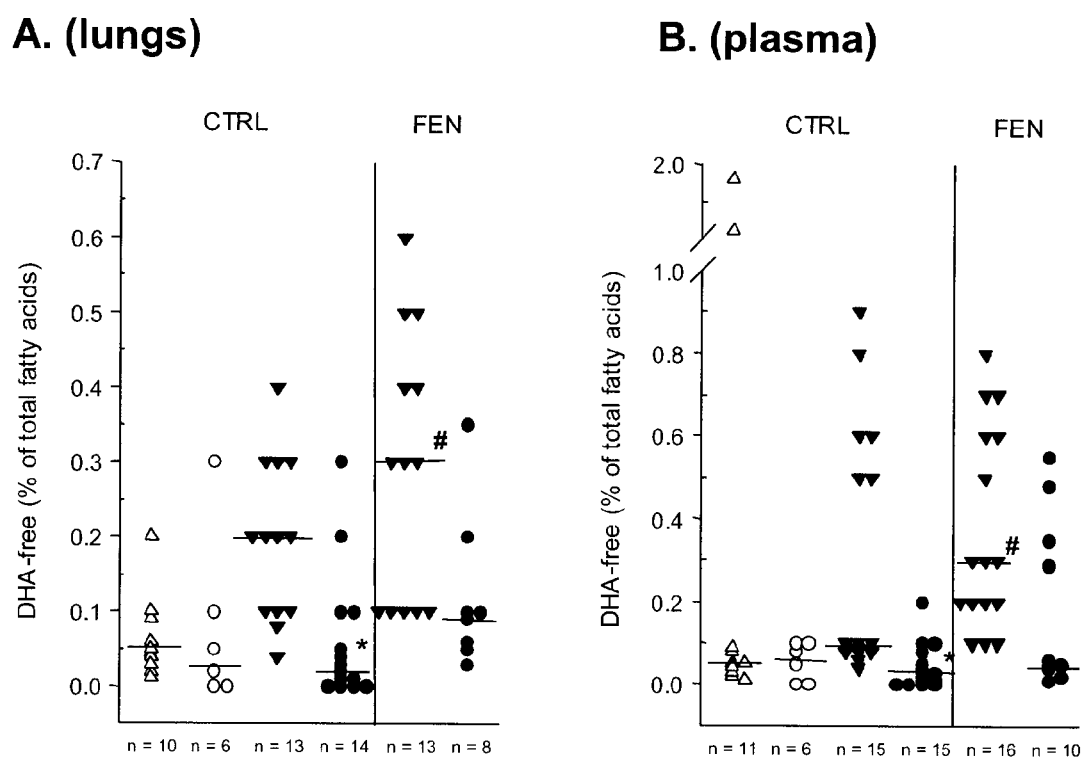
FIG. 8 shows free DHA expressed as percentage of total fatty acids in the lungs and plasma. DHA levels in the lungs (FIG. 8A) and in the plasma (FIG. 8B) were assessed in wild-type (triangles) and Cftr-KO (circles) mice which were not-infected (open) or P. aeruginosa-infected (closed) at 3 days post-infection and that were either not treated or mock-treated (CTRL) or treated with fenretinide (FEN). The fenretinide-treated infected wild-type mice showed a significant difference (#) in the median DHA levels in the lungs and plasma compared to the wild-type untreated uninfected control mice.

Free DHA levels were also analyzed. The median DHA percentile levels in the lungs (p≤0.001) and in the plasma (p≤0.001) samples were statistically different between the groups of mice tested (FIG. 8). The Cftr-KO *P. aeruginosa*-infected mice showed lower median (*) DHA levels compared to their wild-type infected controls in both the lungs and the plasma (FIG. 8, CTRL panels). The fenretinide-treated infected wild-type mice showed a significant difference (#) in the median DHA levels in the lungs and plasma compared to the wild-type untreated uninfected control mice.

Figure 9:
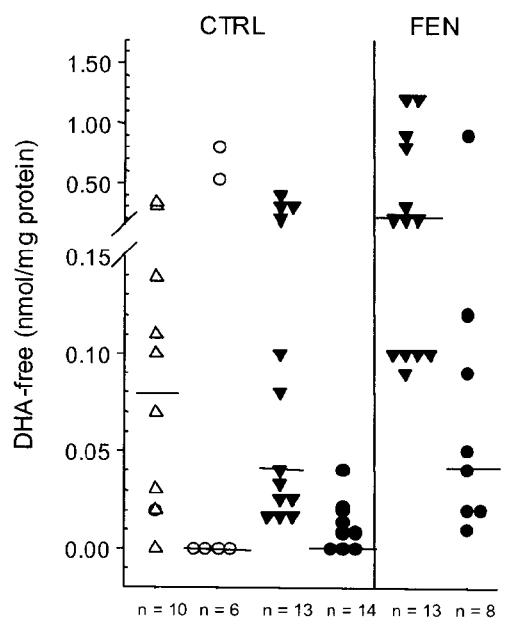
FIG. 9 shows the concentration of free DHA in the lungs and plasma. DHA levels in the lungs (FIG. 9A) and in the plasma (FIG. 9B) were assessed in wild-type (triangles) and Cftr-KO (circles) mice which were not-infected (open) or P. aeruginosa-infected at 3 days post-infection (closed) and that were either not treated and mock-treated (CTRL) or treated with fenretinide (FEN).
Figure 9:
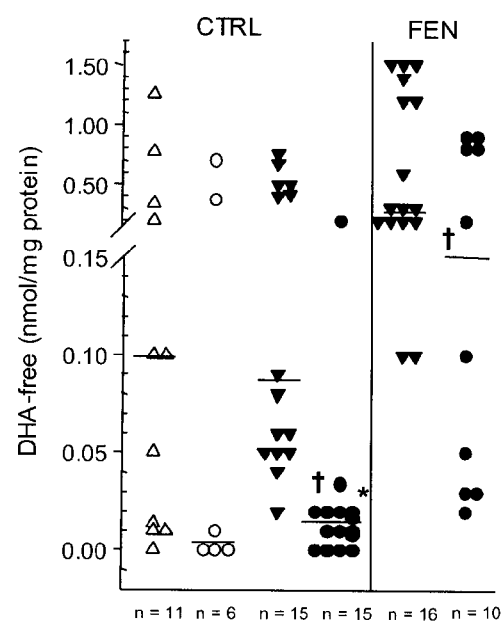

Also, the median DHA concentration levels in the plasma samples were statistically different between the groups of mice tested (FIG. 9, p≤0.001). The Cftr-KO infected mice showed lower median (*) DHA levels compared to their wild-type infected controls in the plasma (FIG. 9, CTRL panels). The fenretinide-treated Cftr-KO infected mice showed higher median (*) DHA levels in the plasma compared to their wild-type infected controls.

Figure 10:
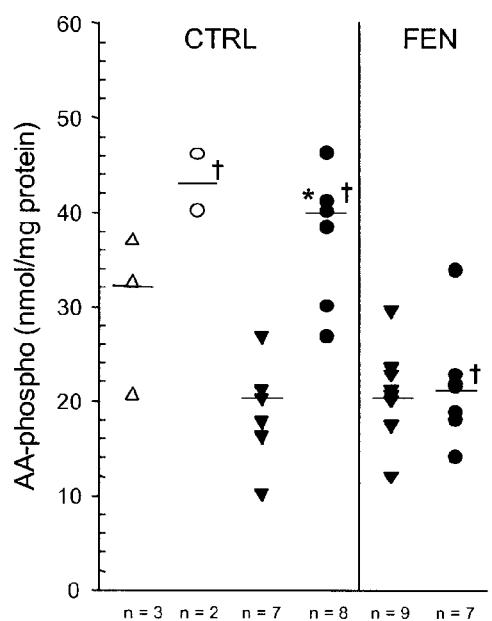
FIG. 10 shows the concentration of AA incorporated in phospholipids. AA levels in the lungs (FIG. 10A) and in the plasma (FIG. 10B) were assessed in wild-type (triangles) and Cftr-KO (circles) mice which were not-infected (open) or P. aeruginosa-infected at 3 days post-infection (closed) and that were either not treated or mock-treated (CTRL) or treated with fenretinide (FEN).
Figure 10:
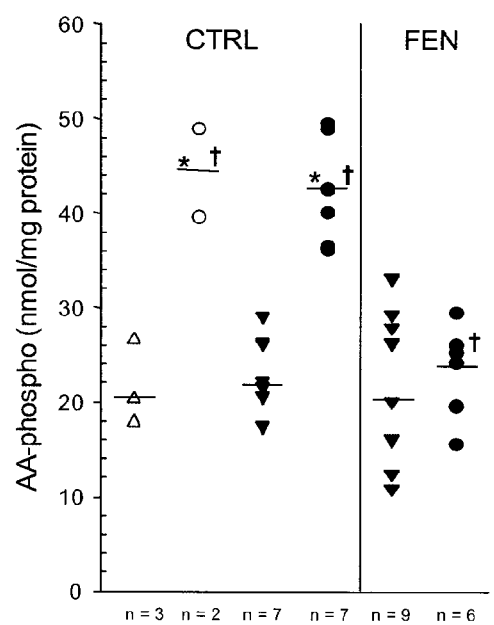

The median AA levels in the lungs (p≤0.001) and in the plasma (p≤0.001) samples were statistically different between the groups of mice tested. The Cftr-KO uninfected mice showed higher median (*) AA levels compared to their wild-type uninfected controls in the plasma samples only (FIG. 10). The Cftr-KO infected mice showed higher median (*) AA levels compared to their wild-type infected controls in both the lungs and the plasma (FIG. 10, CTRL panels). The fenretinide-treated Cftr-KO infected mice showed lower median (*) AA levels compared to their infected Cftr-KO untreated controls both in the lungs and the plasma. In addition to a decrease in AA levels of the lung and plasma, Cftr-KO mice also exhibited a decrease in AA levels in the ileum, liver and pancreas.

Example 7

Effect of Fenretinide on Trabecular Bone Density

Figure 11:
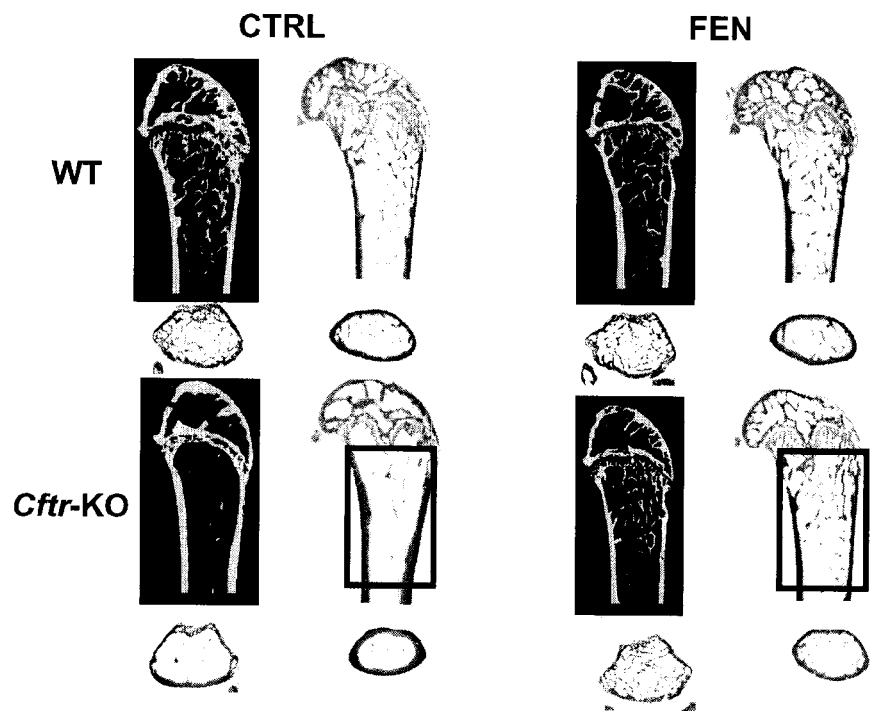
FIG. 11 shows the bone density of wild-type and Cftr-KO mice. A. µCT image of femur. Bones were dissected free of soft tissue, fixed overnight before scanned on a Skyscan 1072 static instrument equipped with 3D Creator analytical software. Representative 3D reconstructions and 2D cross-sectional scans demonstrate a clear difference between control WT and Cftr-KO mice. Cftr-KO mice have much less bone volume then their WT controls. Highlighted by black boxes indicates the area of the bone where µCT was used to scan and displays fenretinide's positive affect in increasing Cftr-KO bone volume. B. von Kassa stains of femur. Bones were embedded in MMA and stained with von Kassa. von Kassa-stained slides were used to confirm the amount of mineralized bone (black stain) to the µCT images. Highlighted by black boxes indicates the area of the bone where µCT was used to scan and displays fenretinide's positive affect in increasing Cftr-KO bone volume. A representative slide is shown.
Figure 11:
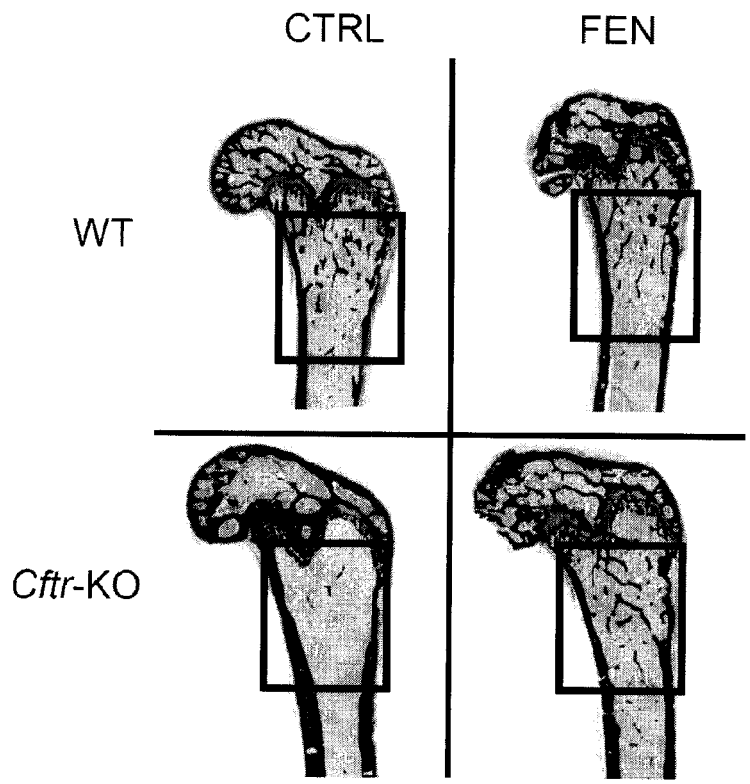

Osteoporosis is characterized by a decrease in the quantity (amount of bone) and quality (structural integrity) of the trabecular bone. FIG. 11 depicts the µCT analysis of the trabecular bones isolated from CF mice and their litter mate controls and it shows that the Cftr-KO mice display clear signs of osteoporosis. These results also clearly demonstrate that biweekly treatment with fenretinide over the course of four weeks (total 8 doses) is able to completely eliminate any signs of osteoporosis in the trabecular bone of Cftr-KO mice. Representative 3D reconstructions and 2D cross-sectional scans demonstrate that, before fenretinide treatment, Cftr-KO mice have little to no trabecular bone highlighted in red boxes evident in the cross-sectional image as compared to littermate controls. After treatment with fenretinide there is a dramatic increase in trabecular bone in the Cftr-KO mice compared to their WT controls.

Example 8

Effect of Fenretinide on Bone Composition and Architecture

Figure 12:
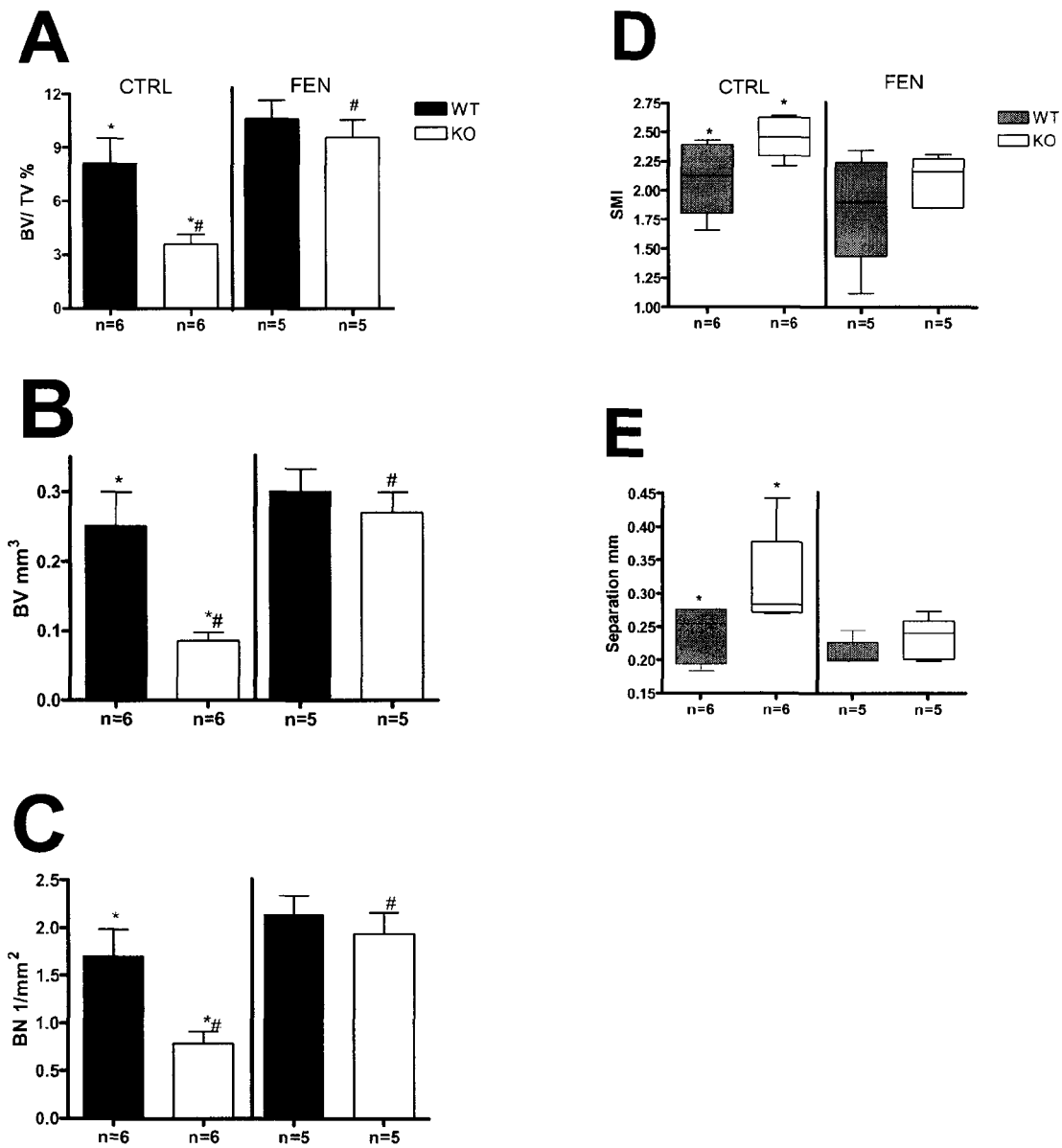
FIG. 12 shows quantitative µCT of Trabecular Bone Composition and Architecture. The following parameters were calculated on the left femur of 5 to 6 mice per group using 3D Creator software supplied with the Skyscan instrument. Lines represent the mean. Significance is set at p<0.05. (*) indicates significance between untreated WT and untreated Cftr-KO and (#) indicates a significant difference found between the Cftr-KO control and treated groups. A. Bone volume/tissue volume. B. Bone volume, C. Trabeculae bone number D. Structure model index, E. Trabeculae Separation; A clear difference is observed between the WT and Cftr-KO control groups, as shown through panels A to E, fenretinide is then shown to increase the BV/TV, BV, BN, SMI and Trb. Sp to the level of the control groups.

To address the osteoporotic changes from the composition and architecture, the trabecular bone was quantified. The following parameters: bone volume/tissue volume (BV/TV), structural model index (SMI) and trabecular separation, were calculated from the left femur. The data presented in FIG. 12A show a statistically significant (p<0.05) reduction in bone volume fraction (BV/TV) in the Cftr-KO mice as compared to WT controls. This is the first demonstration using µCT technology that adult Cftr-KO mice display a significant defect in BV/TV compared to their littermate controls. Interestingly, this difference disappears when Cftr-KO mice are treated with fenretinide (2.7-fold increase), which increases their BV/TV to a level comparable to the levels observed in the WT mice. This increase in BV/TV was associated with a statistically significant increase (p<0.05) in bone volume (BV) and bone number (BN), as shown FIGS. 12B and 12C. Fenretinide treatment increased BV, 3.1-fold and BN, 2.4-fold compared to Cftr-KO mice not treated. The SMI is an algorithm taking into account the change in surface area for the change in radial expansion of trabecular plate-like and rod-like structures, which is known as the "trabecular bone pattern factor" (Wehrli, F. W. et al., 2001. Adv. Exp. Med. Biol. 496:153-64; Wehrli, F. W. et al. 2001. J. Bone Miner. Res. 16:1520-1531). A score is given between 1 and 3 as the value approaches 3 the quality of the bone worsens. FIG. 12D illustrates SMI scores are significant (p=0.026) difference between WT and Cftr-KO untreated mice. However, when these mice are treated with fenretinide, there is no significant (p=0.320) difference between the WT and Cftr-KO. Additionally, separation between the trabecular bones were measured as shown in FIG. 12E, was also measured. Cftr-KO mice have a significantly (p=0.026) higher degree of separation compared to WT controls. When mice are treated with fenretinide there is no longer a significant difference between the trabecular separation (p=0.548). These results suggest that fenretinide not only corrects the quantity of bone but also the quality of the bone structure as well.

The above results were confirmed by analyzing the lumbar vertebrae (V3-V5), which are rich in trabecular bone (data not shown). The µCT results were again confirmed by histomorphometry by staining the femurs with von Kassa stain, which stains mineralized bone in black as shown in FIG. 11B.

Example 9

Effect of Fenritinide on Osteoblast Formation

Figure 13:
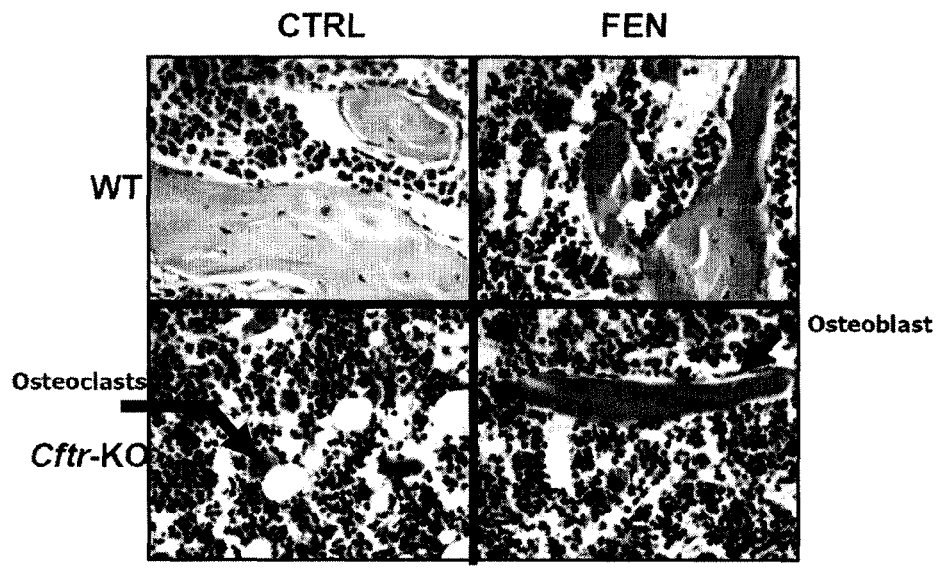
FIG. 13 shows osteoblast and osteoclasts quantification in femur. A. Bones were decalcified, embedded in paraffin and stained with H&E. Multiple slides were used to count the number of osteoblasts and osteoclasts (a representative slide is shown). Slides were counted at 400× magnification. Osteoblasts were identified as single-nucleated, rod shaped cells attached to the trabecular bone as shown by black arrow. Osteoclasts were defined as large multinuclear round (macrophage type) cells attached to the trabecular bone as shown by arrows. B. Quantification of the Counted Slides. Data is shown as the mean+/– the SEM, (*) indicates significance between untreated WT and Cftr-KO mice and (#) indicates a significant difference between the Cftr-KO untreated and treated groups. Data shown are representative of an average of 3 slides counted per animal. C. TRAP Staining. Bones were embedded in MMA and stained with TRAP. Multiple slides were analyzed to identify and quantify osteoclasts present in each slide (a representative slide is shown at 200× magnification).
Figure 13:
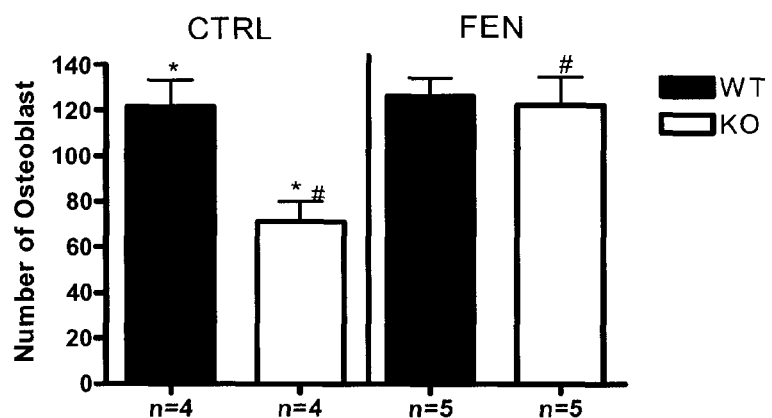
Figure 13:
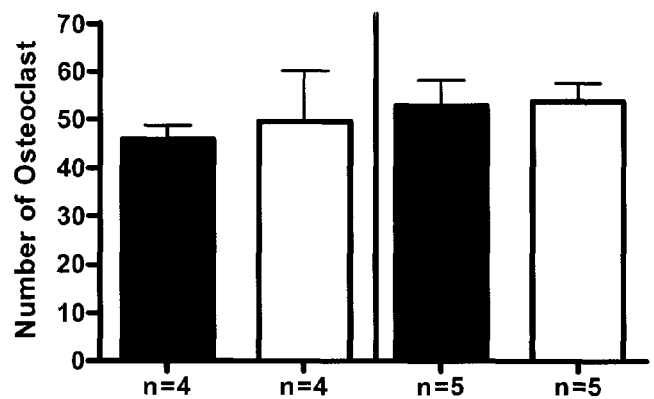
Figure 13:
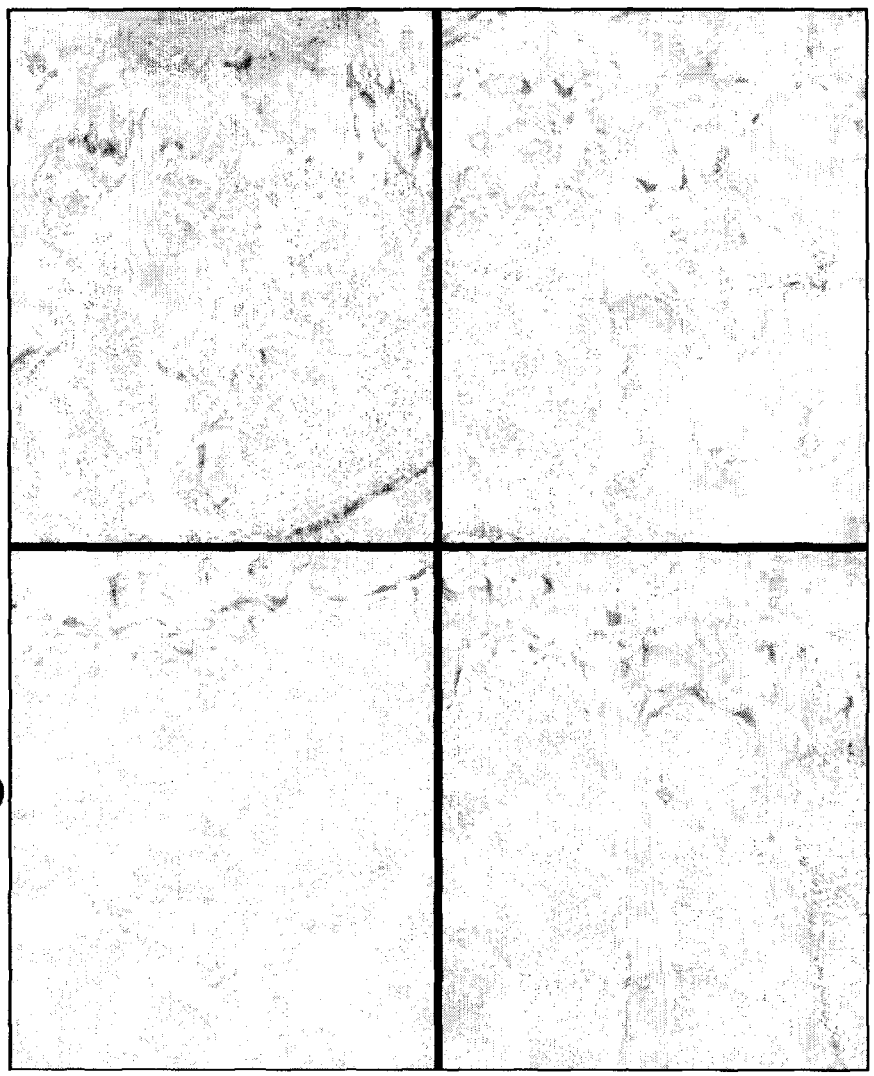

Osteoblasts lay down on new bone lamellae and are active in bone development and also in bone remodelling. In contrast, osteoclasts have been shown to be involved in bone resorption, by digesting the adjacent bone matrix. To establish whether the increase in bone volume observed in the fenretinide treated Cftr-KO mice is the result of more efficient bone formation or of less efficient bone resorption, Applicant counted the number of osteoblasts (bone forming cells) and osteoclasts (bone resorption cells) in the femur. FIG. 13A shows a representative H&E stained slide used to quantify the number of osteoblasts and osteoclasts. FIG. 13B shows the quantification of the average of 3 slides counted per animal in each group. Applicant's analysis clearly demonstrates a striking difference in the number of osteoblasts between the Cftr-KO and WT mice ($p<0.05$). Interestingly, our data also demonstrate that treatment with fenretinide leads to an increase in the amount of osteoblasts for the Cftr-KO mice treated compared Cftr-KO mice that were not treated with fenretinide ($p<0.05$). No significant difference in number of osteoclasts was found between the fenretinide treated and untreated Cftr-KO and WT, (FIG. 13C). This finding was corroborated using TRAP staining, as shown as FIG. 13C, where darker grey spots indicate positive staining for tartrate-resistant acidic phosphatase, an enzyme that is specific for osteoclasts cells.

Example 10

Effect of Fenritinide on Essential Fatty Acid Profiles

Figure 14:
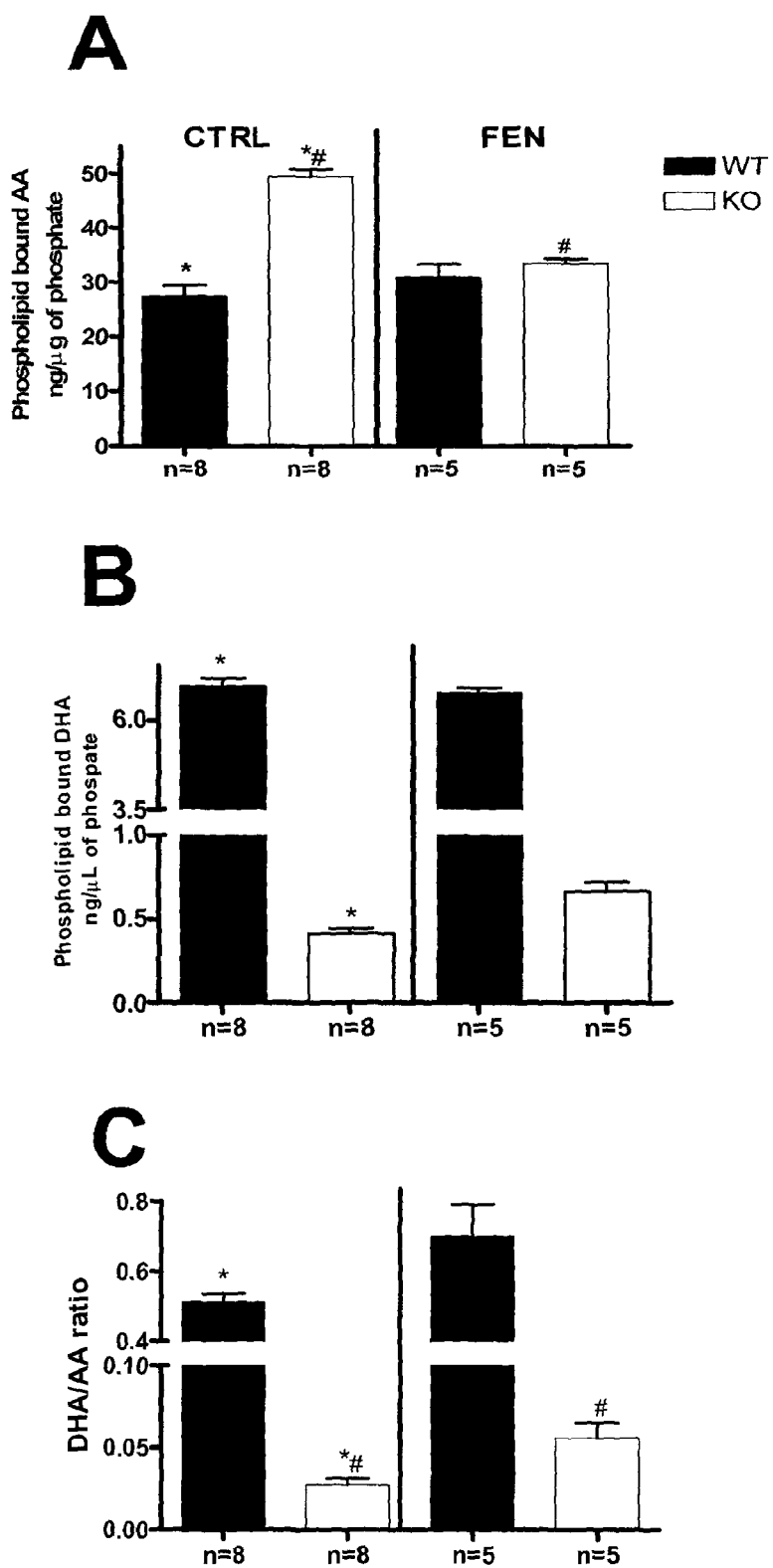
FIG. 14 shows lipid profile of Cftr-KO and WT mice untreated and treated with fenretinide. A. Phospholipid-bound Arachidonic acid. The levels of phospholipid-bound arachidonic acid were quantified in the plasma of WT and Cftr-KO mice. Data is shown as the mean+/– the SEM (*) indicates significance between untreated WT and untreated Cftr-KO and (#) indicates a significant difference found between the Cftr-KO untreated and treated groups. After 4 weeks of biweekly treatment with fenretinide (total of 8 treatments), phospholipid-bound arachidonic acid in the Cftr-KO mice was decreased significantly ($p<0.05$) to the level observed in the WT. A significant difference between treated Cftr-KO animals and WT animals was no longer detectable ($p>0.05$). B. Phospholipid-bound DHA. Concentration of DHA bound in phospholipids was assessed in WT and Cftr-KO mice. (*) indicates significance between untreated WT and untreated Cftr-KO and (#) indicates a significant difference found between the Cftr-KO untreated and treated groups. After 4 weeks of biweekly treatments with fenretinide, DHA bound in phospholipids in WT and Cftr-KO mice increased 2-fold, illustrating a positive trend. C. Phospholipid-bound DHA:AA. The DHA:AA ratio was assessed in WT and Cftr-KO mice. (*) indicates significance between untreated WT and untreated Cftr-KO and (#) indicates a significant difference found between the Cftr-KO untreated and treated groups. The DHA:AA ratio is statistically different between WT and Cftr-KO mice ($p<0.05$). After 4 weeks of biweekly treatments with fenretinide, the ratio of phospholipid-bound DHA and phosholipid-bound AA increases significantly ($p<0.05$).

Remarkably, after 8 treatments (i.e. biweekly administration for 4 weeks) with fenretinide, the concentration of AA in the plasma of Cftr-KO mice was brought down significantly ($p<0.05$) as compared to the WT controls (FIG. 14A). Applicant has demonstrated above (Example 6) that 28 daily treatments with fenretinide completely normalize the lipid imbalance observed in Cftr-KO mice. The data presented in FIG. 14A complement these findings by showing that only 8 (as opposed to 28) treatments with fenretinide effectively reduce the excessive amount of phospholipid-bound AA consistently found in the plasma of Cftr-KO mice. When analyzing the concentration of phospholipid-bound DHA (FIG. 14B), Applicant found a statistically significant increase ($p<0.05$) after fenretinide treatment in both WT and Cftr-KO mice. A positive trend was seen with the fenretinide treatment where a 2-fold increase in phospholipid-bound DHA in Cftr-KO mice, compared to the control Cftr-KO mice. Hence, comparing Cftr-KO untreated animals to the control Cftr-KO treated mice, there was a significant increase ($p<0.05$) in the DHA:AA ratio, as shown in FIG. 14C, where a 2-fold increase is evident.

Example 11

Effect of Fenritinide on Ceramide Concentrations

Figure 15:
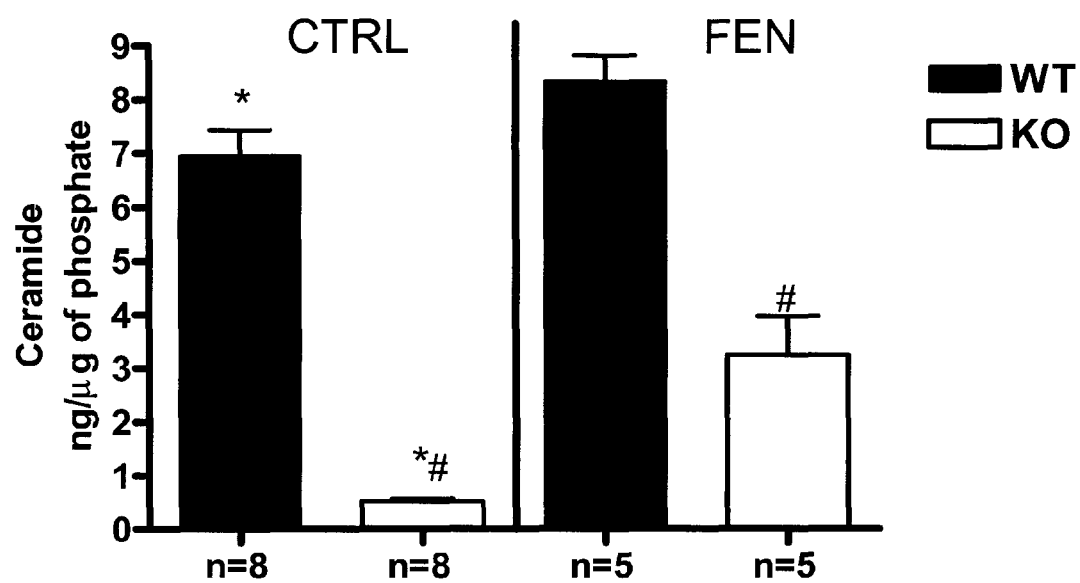
FIG. 15 shows ceramide-sphingolipids levels in Cftr-KO and WT mice untreated and treated with Fenretinide. Ceramide levels were assessed in plasma isolated from WT and Cftr-KO mice. The ceramide levels in the plasma samples were statistically different ($p<0.05$ (*)) between WT and Cftr-KO mice. Following 4 weeks of biweekly treatment with fenretinide, the ceramide levels in the Cftr-KO mice increased significantly [$p<0.05$ (#)].

Applicant has shown above (Example 2) that ceramide levels are dramatically diminished in Cftr-KO mice, and that this impairment can be corrected with 28 days of fenretinide treatment, Applicant assessed whether only 8 treatments with fenretinide would correct this impairment as well. Ceramide levels in the untreated Cftr-KO mice, as compared to their WT littermate controls, were statistically significantly lower ($p<0.05$) (FIG. 15, left panel). After 4 weeks of biweekly treatment with fenretinide, the ceramide levels in the treated Cftr-KO mice 5.9-fold increase compared to untreated Cftr-KO mice ($p<0.05$) (FIG. 15, right panel).

Example 12

Figure 16:
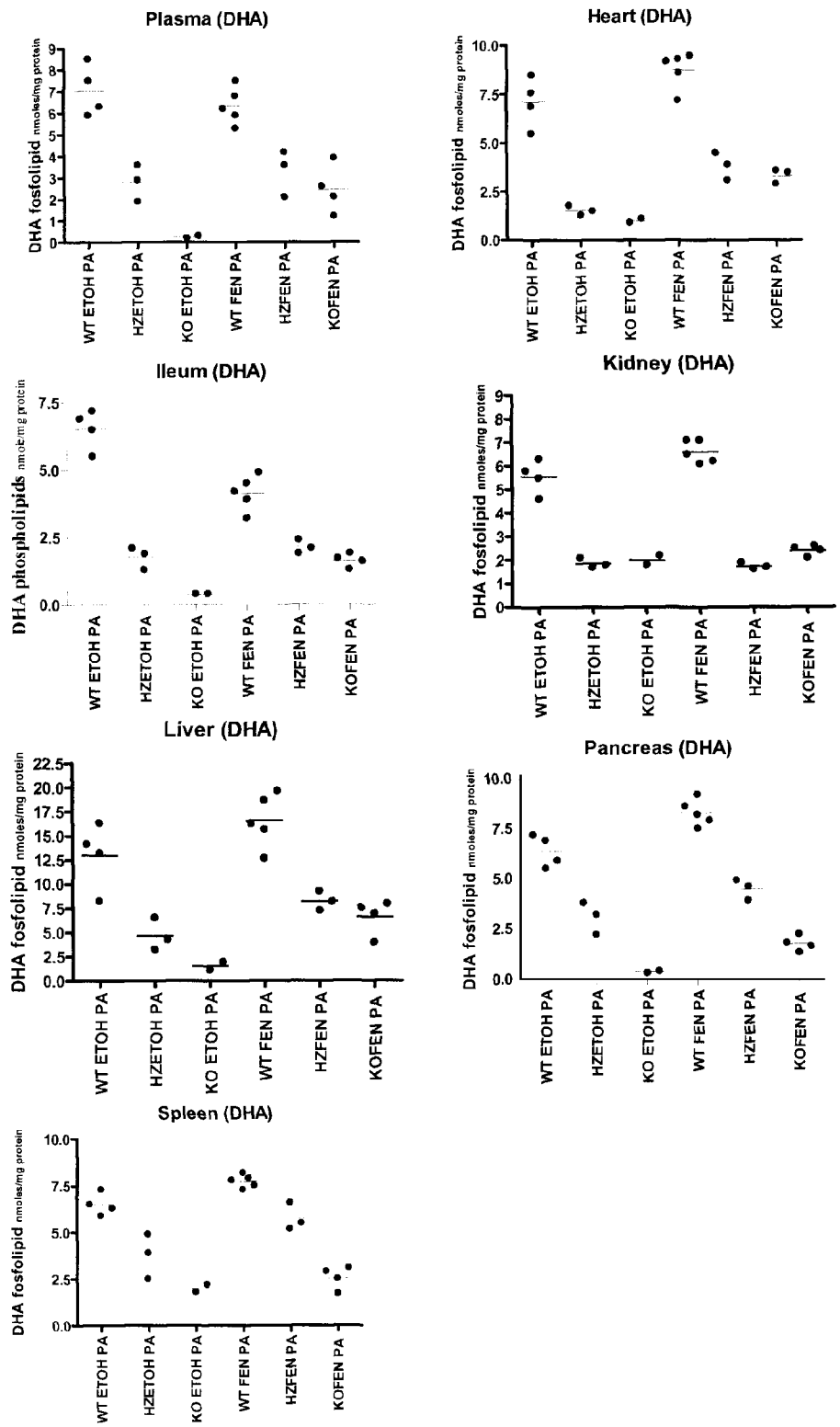
FIG. 16 shows the lipid profile in different organs from Cftr-KO (KO), Cftr heterozygous (HZ) and wild-type (WT) mice following biweekly administration of fenretinide during 4 weeks. A. DHA levels. B. Ceramide levels. C. DHA/AA ratio. D. AA levels. The levels of phospholipid-bound arachidonic acid were quantified in the plasma, liver, pancreas, ileum, spleen, kidney and heart of WT and Cftr-KO mice. After 4 weeks of biweekly treatment with fenretinide (total of 8 treatments), phospholipid-bound arachidonic acid in the Cftr-KO mice was decreased significantly.
Figure 16:
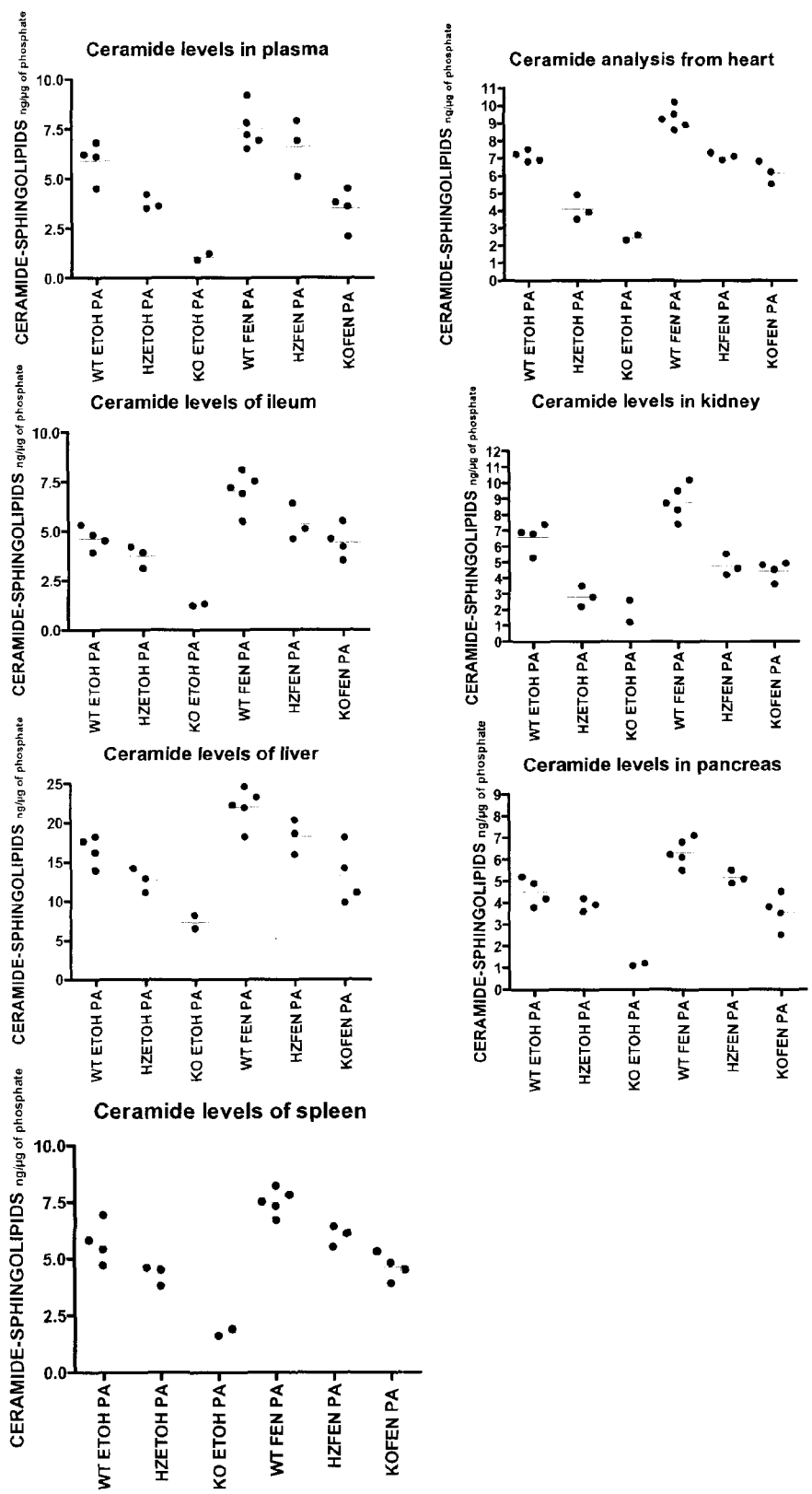
Figure 16:
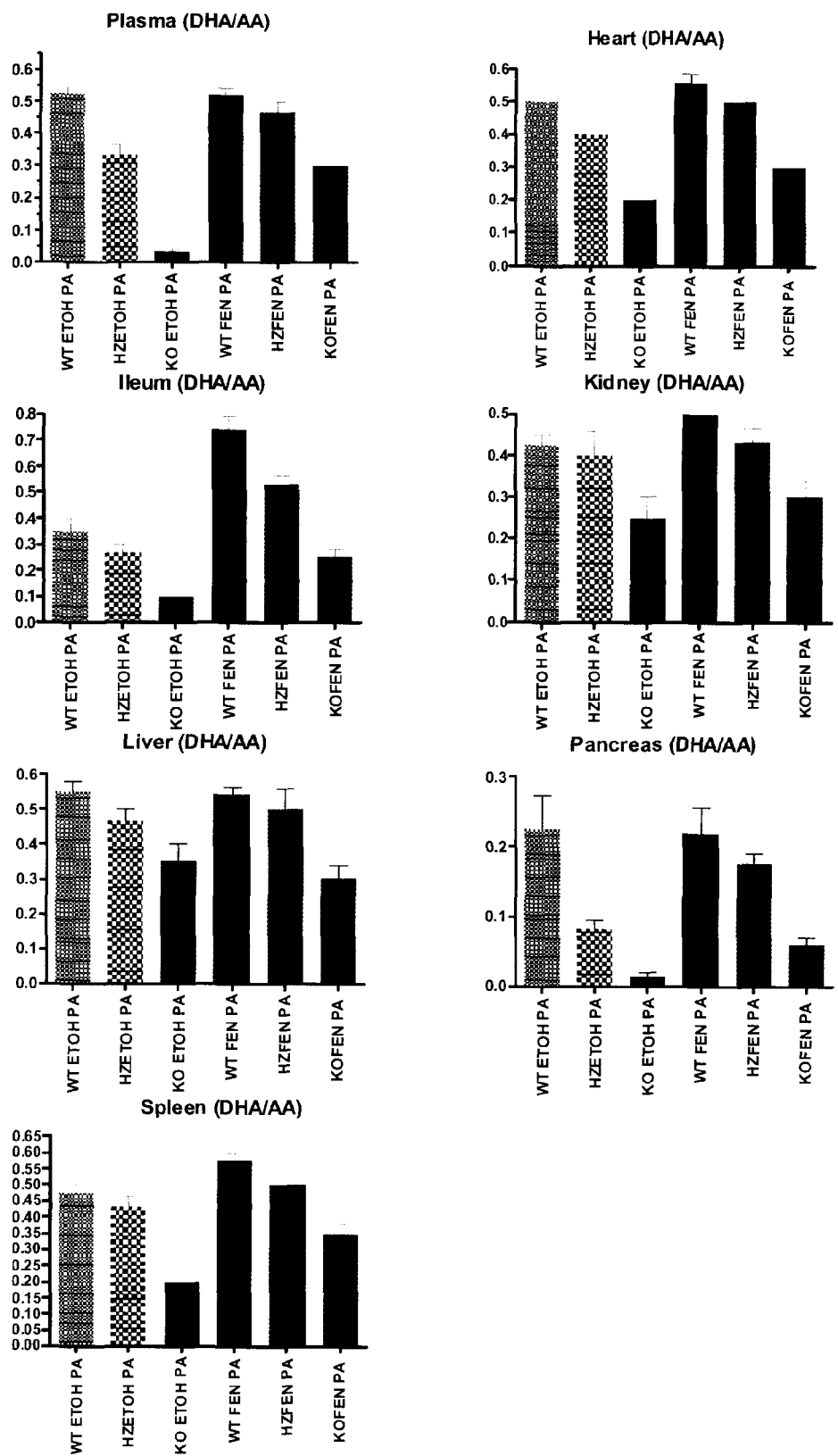
Figure 16:
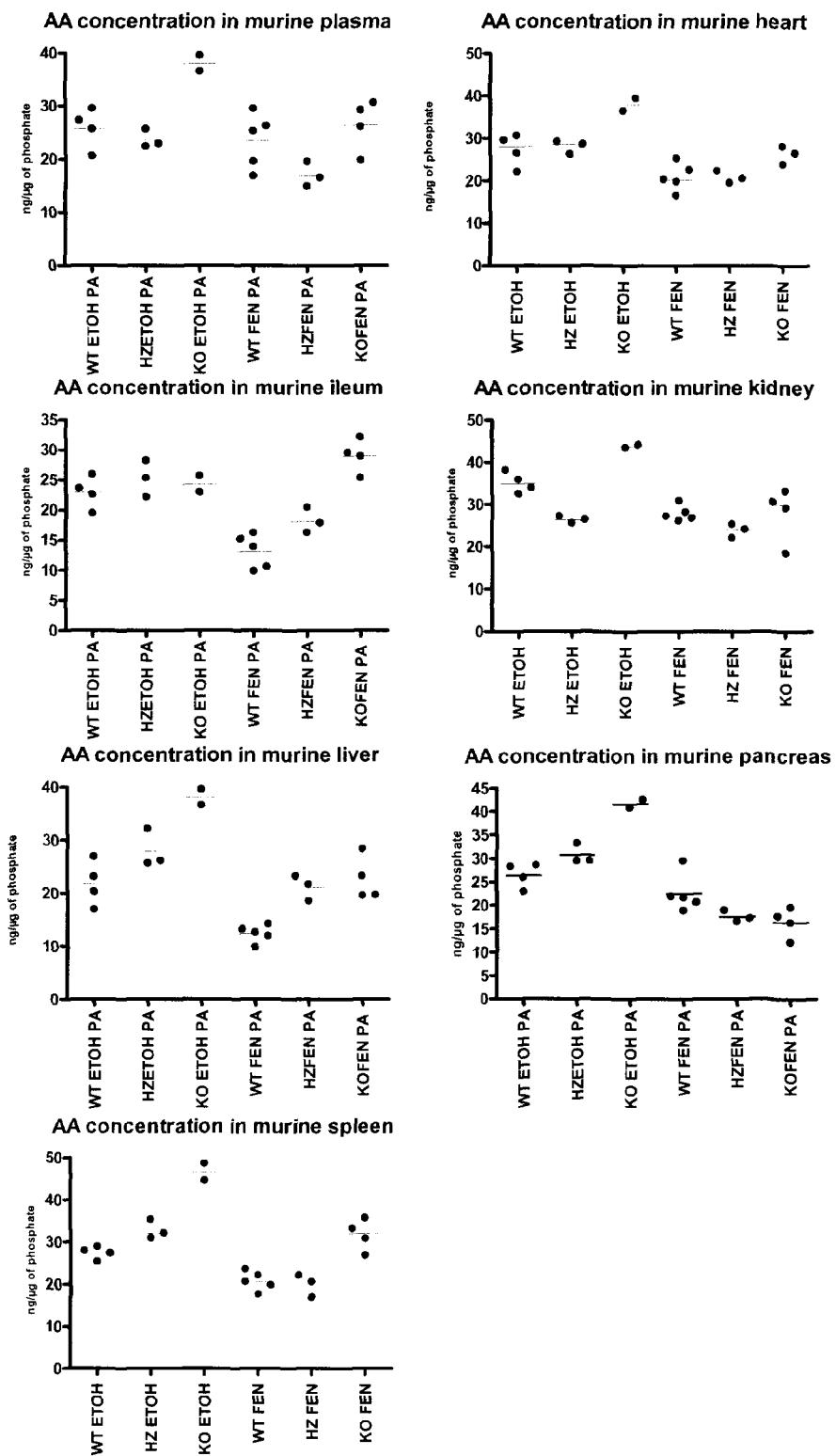

Effect of Low Dose Fenretinide Treatment on Systemic Lipid Parameters in Cftr-KO Mice The data presented in FIG. 16 demonstrates that the lipid imbalance in CF mice is systemic; as compared to their WT counterparts, Cftr-KO mice showed lower DHA levels (FIG. 16A), DHA/AA ratio (FIG. 16B) and ceramide levels (FIG. 16C) in several organs, including in "control" organs (i.e. organs not clinically affected in CF), namely the heart, kidney and spleen. Mice heterozygous for the CFTR gene deletion (HZ) typically showed intermediate DHA and ceramide levels and an intermediate DHA/AA ratio, as compared to WT and Cftr-KO mice. Moreover, a four-week, biweekly treatment with fenretinide was effective at correcting, at least partially, the defect/imbalance in DHA levels, DHA/AA ratio and ceramide levels in all organs from Cftr-KO (KO ETOH vs. KO FEN) and HZ mice (HZ ETOH vs. HZ FEN). FIG. 16D shows that Cftr-KO mice have higher levels of AA (as compared to WT mice) in all control organs tested (heart, kidney and spleen), and that a four-week, biweekly treatment with fenretinide decreases the AA levels to normal (comparable to the AA levels measured in mock-treated WT mice (WT ETOH). These results demonstrate that the lipid imbalance in CF mice is systemic and that a four-week, biweekly treatment with fenretinide can correct the defect in all organs.

Example 13

Lipid Imbalance and CFTR Mutations in Humans

Applicant analyzed lipid parameters in CF patients carrying different mutations at the CFTR gene locus. CF patients were subdivided into three group based on their CF genotype. The first group represents CF patients homozygous for the deltaF508 mutation (ΔF508) at the CFTR locus (deltaF508/deltaF508), which results in the most severe form of the disease. The second group comprises CF patients heterozygous for the deltaF508 mutation and carrying one other somewhat less severe but well characterized mutation at the CFTR locus (deltaF508/other). The third group does not carry a delta F508 mutation at the CFTR gene locus, but carry two other mutations, a combination that is believed to produce somewhat less severe Cystic fibrosis disease (other/other) as some residual CFTR protein level can be detected for some of the mutations, although it is not perfectly quantified. All of patients with deltaF508/deltaF508 share the pancreatic insufficiency, in the group where other mutation combinations are analyzed some patients also show pancreatic insufficiency (e.g. deltaF508/other or other/other (see Table 6).

TABLE 6

CF genotype and pancreatic insufficiency

| Pancreatic Insufficiency Total amount of patients: 47 | | | | Pancreatic Sufficiency Total: 10 patients | |
| --- | --- | --- | --- | --- | --- |
| allele 1 | allele 2 | allele 1 | allele 2 | allele 1 | allele 2 |
| ΔF508 | ΔF508 | ΔF508 | 621 + 1G = T | ΔF508 | R334w |
| ΔF508 | ΔF508 | ΔF508 | 3849 + 10kb C->T | ΔF508 ΔF508 | 711 + 1G--T L206W |
| ΔF508 | ΔF508 | ΔF508 | Y 1092X | ΔF508 | unknown |

TABLE 6-continued

CF genotype and pancreatic insufficiency

| Pancreatic Insufficiency Total amount of patients: 47 | | | | Pancreatic Sufficiency Total: 10 patients | |
|---|---|---|---|---|---|
| allele 1 | allele 2 | allele 1 | allele 2 | allele 1 | allele 2 |
| ΔF508 | ΔF508 | ΔF508 | A455E | ΔF508 | unknown |
| ΔF508 | ΔF508 | ΔF508 | unknown | G85e | G85e |
| ΔF508 | ΔF508 | ΔF508 | W1282X | 621 + 1G > T | L206W |
| ΔF508 | ΔF508 | ΔF508 | G85e | 621 + 1G = T | L206W |
| ΔF508 | ΔF508 | ΔF508 | R334W | unknown | unknown |
| ΔF508 | ΔF508 | ΔF508 | unknown | not tested | not tested |
| ΔF508 | ΔF508 | ΔF508 | unknown | | |
| ΔF508 | ΔF508 | ΔF508 | unknown | | |
| ΔF508 | ΔF508 | ΔF508 | unknown | | |
| ΔF508 | ΔF508 | ΔF508 | unknown | | |
| ΔF508 | ΔF508 | ΔF508 | unknown | | |
| ΔF508 | ΔF508 | ΔF508 | unknown | | |
| ΔF508 | ΔF508 | R334w | unknown | | |
| ΔF508 | ΔF508 | W1282X | W1282X | | |
| ΔF508 | ΔF508 | unknown | unknown | | |
| ΔF508 | ΔF508 | unknown | unknown | | |
| ΔF508 | ΔF508 | unknown | unknown | | |
| ΔF508 | ΔF508 | unknown | unknown | | |
| ΔF508 | ΔF508 | not tested | not tested | | |
| ΔF508 | ΔF508 | | | | |
| ΔF508 | ΔF508 | | | | |
| ΔF508 | ΔF508 | | | | |

Figure 17:
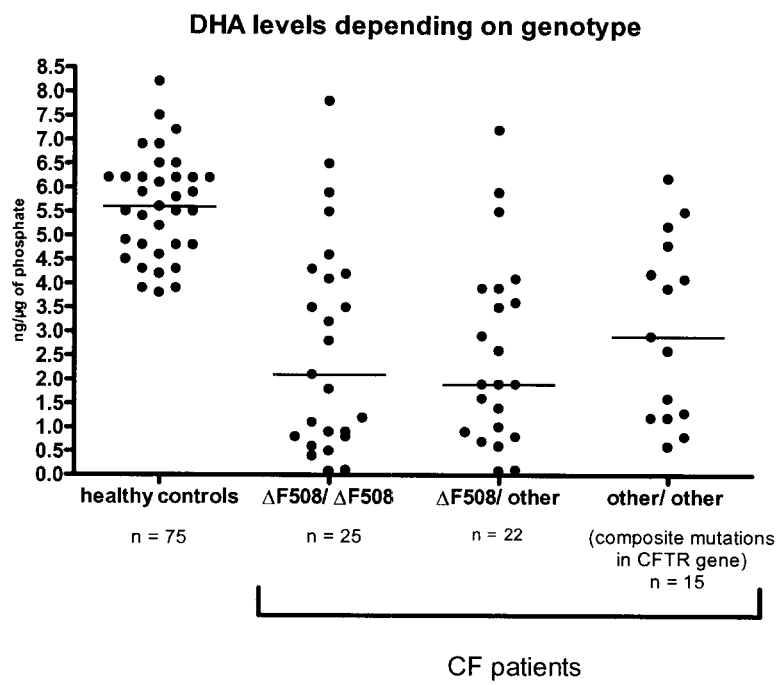
FIG. 17 shows lipid parameters in healthy subjects and in patients with different CF genotypes. Blood samples were collected from 75 healthy volunteers and 62 CF patients. CF patients were subdivided into three group based on their CF genotype. The first group represents CF patients homozygous for the deltaF508 mutation at the CFTR locus (deltaF508/deltaF508), which results in the most severe form of the disease. The second group comprises CF patients heterozygous for the deltaF508 mutation and carrying one other mutation at the CFTR locus (deltaF508/other). The types of the mutations are listed in Table 1. "Unknown" means that a specific mutation was not identified because it has not been one of the 40 mutations that can be identified using the genotyping kit utilized at the Montreal Children Hospital; the patient's sweat test identified patient as CF patient. The third group does not carry a deltaF508 mutation at the CFTR gene locus, but carry two other mutations, a combination that is believed to produce somewhat less severe Cystic fibrosis disease (other/other), as some residual CFTR protein level can be detected for some of the mutations, although it is not perfectly quantified. All of patients with deltaF508/deltaF508 share the pancreatic insufficiency, in the group where other mutation combinations are analyzed some patients also show pancreatic insufficiency (e.g. deltaF508/other or other/other (see Table 6). A. DHA levels. B. AA levels. C. DHA/AA ratio. D. Ceramide levels.
Figure 17:
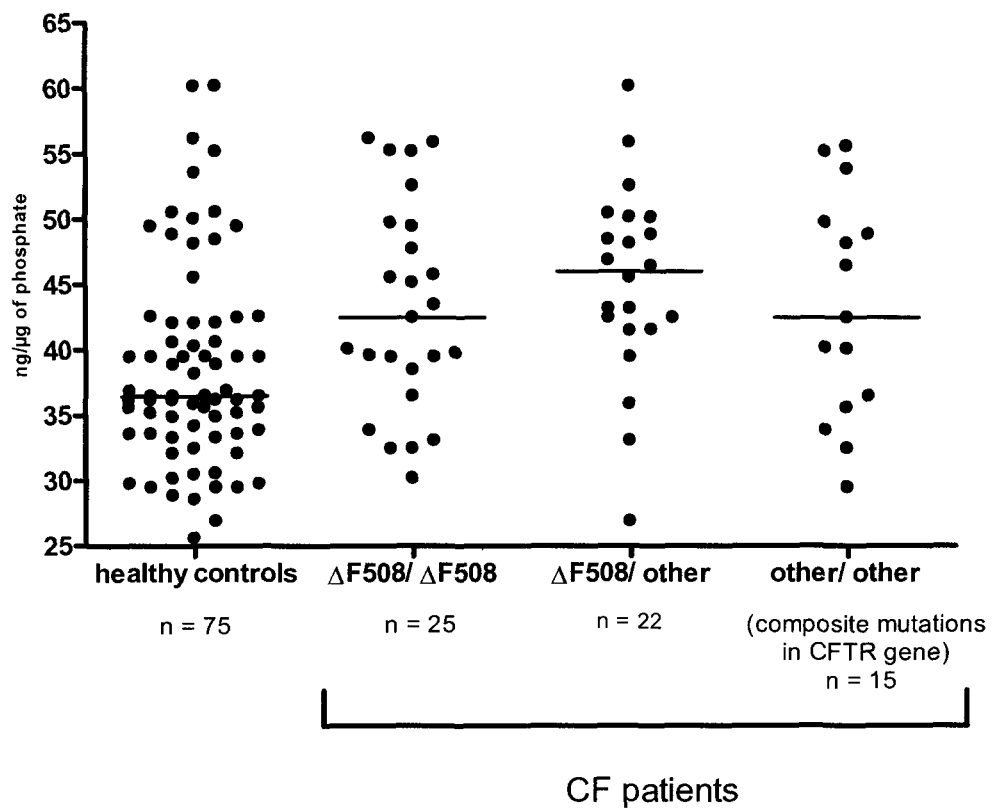
Figure 17:
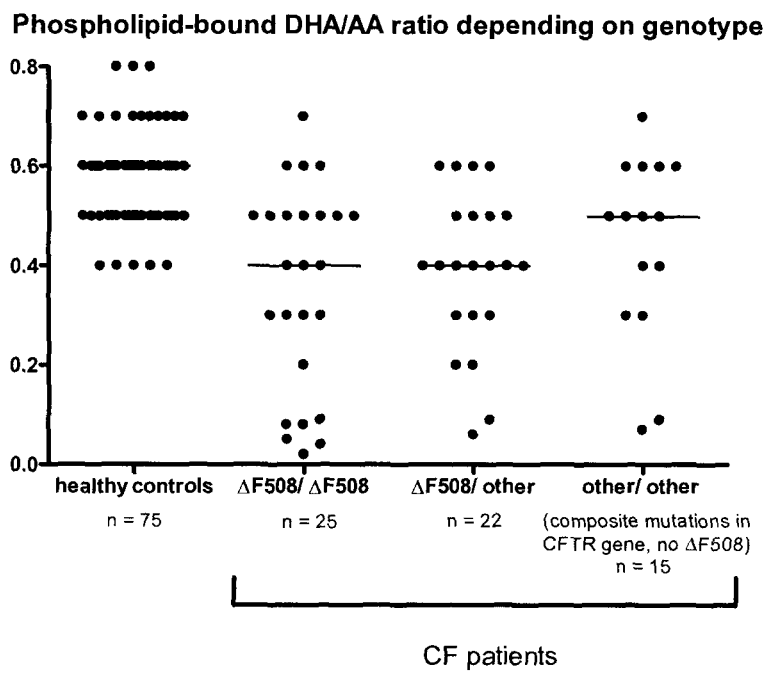
Figure 17:
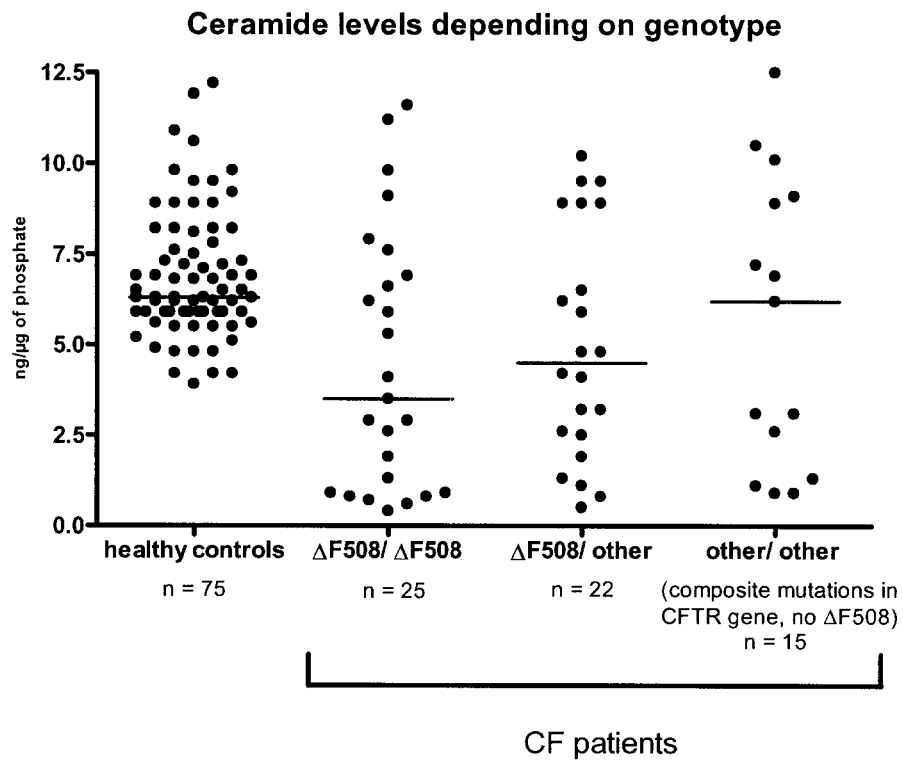

As shown in FIGS. 17A and 17B, lower phospholipids-bound DHA levels and DHA/AA ratio were measured in all groups of CF patients as compared to healthy subjects. Healthy control and CF patients with ΔF508/ΔF508 mutation have a significantly different DHA/AA ratio ($p<0.001$) (FIG. 17B); however, there is no significant difference between the three group of CF patients. Also the healthy controls are significantly different from the ΔF508/other mutation ($p<0.001$), and from CF patients with other/other gene mutation ($p<0.05$). Moreover, only CF patients homozygous for the ΔF508 mutation showed significant lower ceramide levels as compared to healthy subjects ($p<0.05$, FIG. 17C). Also, the data presented in FIG. 17 demonstrate that not all CF patients have a lipid imbalance (i.e. there are important variations between CF patients); even in the group with the most severe form of the disease (ΔF508/ΔF508), some patients have AA, DHA and ceramide levels comparable to the levels measured in healthy subjects.

Although the present invention has been described hereinabove by way of specific embodiments thereof, it can be modified, without departing from the spirit and nature of the subject invention as defined in the appended claims.

What is claimed is:

1. A method of decreasing bacterial load in a subject having a lipid imbalance, said method comprising:
   (i) selecting a subject having a lipid imbalance and suffering from an increased bacterial load; and
   (ii) (a) decreasing arachidonic acid (AA) levels, (b) increasing docosahexaenoic acid (DHA) levels, c) increasing the DHA/AA ratio, or (d) any combination of (a)-(c), by administering to said subject an effective amount of fenretinide or a pharmaceutically-acceptable salt thereof;
   wherein said effective amount of fenretinide or a pharmaceutically-acceptable salt thereof is effective to decrease said bacterial load without increasing the amount and/or activity of inflammatory cells.

2. The method of claim 1, wherein said increase of DHA levels or of the DHA/AA ratio or said decrease of AA levels is systemic.

3. The method of claim 1, wherein said subject suffers from cystic fibrosis.

4. The method according to claim 1, wherein said subject has (a) a DHA/AA ratio of 0.4 or less, (b) DHA levels of 3.5 ng/μg of phosphate or less, (c) AA levels of 40 ng/μg of phosphate or more or (d) any combination of (a) to (c), prior to said administration.

5. The method of claim 1, wherein said increased bacterial load is due to an opportunistic infection.

6. The method of claim 1, wherein said DHA and AA are phospholipid-associated fractions of DHA and AA.

7. The method of claim 1, wherein said subject is a mammal.

8. The method of claim 7, wherein said mammal is a human.

9. The method of claim 1, wherein said increased bacterial load is an increased bacterial load of the respiratory tract.

10. The method of claim 5, wherein said opportunistic infection is *Pseudomonas aeruginosa* infection.

* * * * *